(12) United States Patent
Keusenkothen

(10) Patent No.: US 9,388,094 B2
(45) Date of Patent: Jul. 12, 2016

(54) CATALYTIC ALKANE CONVERSION

(71) Applicant: ExxonMobil Chemical Patents Inc., Baytown, TX (US)

(72) Inventor: Paul F. Keusenkothen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 156 days.

(21) Appl. No.: 14/469,109

(22) Filed: Aug. 26, 2014

(65) Prior Publication Data
US 2015/0065771 A1 Mar. 5, 2015

Related U.S. Application Data

(60) Provisional application No. 61/872,175, filed on Aug. 30, 2013.

(51) Int. Cl.
*C07C 5/327* (2006.01)
*C07C 5/333* (2006.01)
*C07C 2/84* (2006.01)
(Continued)

(52) U.S. Cl.
CPC .................. *C07C 2/84* (2013.01); *B01J 8/0207* (2013.01); *B01J 15/005* (2013.01); *B01J 19/24* (2013.01); *B01J 19/245* (2013.01); *C07C 2/08* (2013.01); *C07C 2/42* (2013.01); *C07C 2/78* (2013.01); *C07C 5/48* (2013.01); *C07C 7/005* (2013.01); *C07C 7/12* (2013.01); *B01D 53/04* (2013.01); *B01D 2256/24* (2013.01); *B01D 2257/7022* (2013.01); *B01D 2259/4009* (2013.01); *B01J 2208/0053* (2013.01); *B01J 2208/00309* (2013.01); *B01J 2208/00548* (2013.01); *B01J 2208/00557* (2013.01); *B01J 2208/00566* (2013.01); *B01J 2219/24* (2013.01); *B01J 2219/2402* (2013.01); *Y02P 20/51* (2015.11)

(58) Field of Classification Search
CPC ................................ C07C 5/327; C07C 5/333
USPC .................... 585/658, 661, 921, 922
See application file for complete search history.

(56) References Cited

U.S. PATENT DOCUMENTS 5,905,180 A 5/1999 Yokoyama et al.
2002/0020113 A1 2/2002 Kennedy et al.
(Continued)

FOREIGN PATENT DOCUMENTS

WO 95/20556 8/1995
WO 02/24614 3/2002
(Continued)

OTHER PUBLICATIONS

*Synthesis of Ethylene via Oxidative Coupling of Methane*, G.E. Keller and M.H. Bhasin, Journal of Catalysis 73, 9-19 (1982).
(Continued)

*Primary Examiner* — Thuan D Dang

(57) ABSTRACT

Disclosed is a hydrocarbon conversion process in which an alkane component is catalytically converted in the presence of an oxygen or oxidizing component (i.e., oxidant). The hydrocarbon conversion process can be an oxidative coupling reaction, which refers to the catalytic conversion of alkane in the presence of oxidant to produce an olefin product, i.e., a composition containing $C_{2+}$ olefin. Reverse-flow reactors can be used to carry out the oxidative coupling reaction.

12 Claims, 5 Drawing Sheets

(51) Int. Cl.
- *C07C 7/12* (2006.01)
- *B01J 8/02* (2006.01)
- *C07C 2/42* (2006.01)
- *B01J 19/24* (2006.01)
- *C07C 2/08* (2006.01)
- *C07C 5/48* (2006.01)
- *C07C 7/00* (2006.01)
- *B01J 15/00* (2006.01)
- *C07C 2/78* (2006.01)
- *B01D 53/04* (2006.01)

(56) References Cited

U.S. PATENT DOCUMENTS

| | | |
|---|---|---|
| 2005/0113247 A1 | 5/2005 | Chen et al. |
| 2015/0065767 A1 | 3/2015 | Henao et al. |
| 2015/0065769 A1 | 3/2015 | Henao et al. |
| 2015/0065773 A1 | 3/2015 | Henao et al. |

FOREIGN PATENT DOCUMENTS

| | | |
|---|---|---|
| WO | 2007/028153 | 3/2007 |
| WO | 2007/075945 | 7/2007 |

OTHER PUBLICATIONS

*Enhanced $C_2$ Yields from Methane Oxidative Coupling by Means of a Separative Chemical Reactor*, A.E. Tonkovich, R.W. Carr, R. Aris, Science 262, 221-223( 1993).

*Methane to Ethylene with 85 Percent Yield in a Gas Recycle Electrocatalytic Reactor-Separator*, Y. Jiang, I.V. Yentekakis, C.G. Vayenas, Science 264, 1563-1566 (1994).

Mleczko, L. et al. "*Catalytic oxidative coupling of methane—reaction engineering aspects and process schemes*", Fuels Processing Technology, Elsevier, 42, 217-248 (1995).

Liu, T. et al., "*Autothermal Reforming of Methane in a Reverse-Flow Reactor*", Chem. Eng. Technol., Wiley VCH 32, No. 9, 1358-1366 (2009).

Veser, G. "*Multiscale process intensification for catalytic partial oxidation of methane: From nanostructured catalysts to integrated reactor concepts*", Catalysis Today, Elsevier, 157, 24-32 (2010).

Korf, S.J. et al. "*The Development of Doped Li/MgO Catalyst Systems for the Low-Temperature Oxidative Coupling of Methane*", Methane Conversion by Oxidative Processes—Fundamental and Engineering Aspects, Van Nostrand Reinhold/Springer, 168-199 (1992).

T.P. Tiermersma et al. "A novel autothermal reactor concept for thermal coupling of the exothermic oxidative coupling and endothermic steam reforming of methane", Chem. Eng. Journal. vol. 203,Sep. 1, 2012, pp. 223-230.

Mortazavi et al., "Catalytic Methane Coupling Under Periodic Operation", The Canadian Journal of Chemical Engineering, vol. 74, No. 5, Oct. 1, 1996, pp. 683-694.

CATALYTIC ALKANE CONVERSION

CROSS REFERENCE TO RELATED APPLICATIONS

This application claims priority to and the benefit of (i) U.S. Provisional Patent Application No. 61/872,175, filed Aug. 30, 2013; (ii) E.P. Patent Application No. 13189746.4, filed Oct. 22, 2013; the contents of which are incorporated herein by reference in their entireties. The following related cases are also incorporated by reference in their entireties: (i) P.C.T. Patent Application No. PCT/US2014/052710, filed Aug. 26, 2014; (ii) U.S. patent application Ser. No. 14/469,141, filed Aug. 26, 2014, (iii) P.C.T. Patent Application No. WO2015/031366, filed Aug. 26, 2014; (iv) U.S. patent application Ser. No. 14/469,180, filed Aug. 26, 2014; (v) P.C.T. Patent Application No. PCT/US2014/052722, filed Aug. 26, 2014; (vi) U.S. patent application Ser. No. 14/469,227, filed Aug. 26, 2014; and (vii) P.C.T. Patent Application No. PCT/US2014/052698, filed Aug. 26, 2014.

FIELD OF THE INVENTION

The invention relates to processes for catalytically converting alkane. The invention further relates to processes for catalytically converting alkane to produce $C_{2+}$ unsaturates, and to equipment useful in such processes.

BACKGROUND OF THE INVENTION

Producing ethylene by methane dehydrogenation is an energy-intensive reaction. Since the reaction is endothermic and reaction temperatures greater than 800° C. are generally required to achieve practical methane conversion levels, a significant amount of heat is required to maintain the reaction. Generating this heat and transferring it to the methane is a significant cost, and can introduce inefficiencies into the process. In order to overcome some of these difficulties, there has been considerable effort directed toward methane conversion via catalytic oxidative coupling reactions.

One process for producing ethylene from methane by catalytic oxidative coupling is disclosed in *Synthesis of Ethylene via Oxidative Coupling of Methane*, G. E. Keller and M. H. Bhasin, Journal of Catalysis 73, 9-19 (1982). Although an appreciable selectivity to ethylene was observed (to a maximum of about 50%), conversion was relatively low. In order to overcome the methane-ethylene separation difficulties resulting from the low methane conversion, technology has been developed for quenching the reaction product downstream of the oxidative coupling reactor, and then separating ethylene from the unreacted methane.

One process, disclosed in *Enhanced $C_2$ Yields from Methane Oxidative Coupling by Means of a Separative Chemical Reactor*, A. E. Tonkovich, R. W. Carr, R. Aris, Science 262, 221-223, 1993, includes a simulated countercurrent moving-bed chromatographic reactor, and achieves 65% methane conversion and 80% selectivity to $C_2$ hydrocarbons. The reactor is configured in four sections, with each section comprising (i) a catalytic reactor containing $Sm_2O_3$ catalyst and (ii) an adsorbent column located downstream of the catalytic reactor. Methane and oxygen react via catalytic oxidative coupling in the reactor at a temperature in the range of about 900° K to 1100° K, and then ethylene is separated from unreacted methane in the sorption column. In order to maintain sufficient selectivity for ethylene sorption, the reactor's product is quenched to a temperature of 373° K in the sorption column. In another process, disclosed in *Methane to Ethylene with 85 Percent Yield in a Gas Recycle Electrocatalytic Reactor-Separator*, Y. Jiang, I. V. Yentekakis, C. G. Vayenas, Science 264, 1563-1566, 1994, gas recycle is utilized to further increase methane conversion, but an even lower quench temperature (30° C.) is used during ethylene sorption.

Although the disclosed moving-bed and gas-recycle processes improve conversion, the quenching is energy intensive, and further improvements are desired. Further improvements are particularly desired in converting alkanes such as methane into $C_{2+}$ olefins such as ethylene and propylene, particularly with increasing selectivity to ethylene production.

SUMMARY OF THE INVENTION

This invention provides a hydrocarbon conversion process that is less energy intensive than comparable processes. The hydrocarbon conversion process is particularly desirable for converting alkanes such as methane into $C_{2+}$ olefins such as ethylene and propylene, especially with increasing selectivity to ethylene production.

More particularly, the invention relates to a process for catalytically converting alkane and oxidant to olefin. The process can be carried out in a flow-through reactor, e.g., a tube reactor. The flow-through reactor comprises catalyst and at least one thermal mass. Hydrogen catalytically transfers from the alkane to the oxidant to produce a reaction mixture, which is then quenched in the reactor by contacting the reaction mixture with the thermal mass. The thermal mass is cooled after the quenching. The process can be operated continuously by repeating the catalytic transfer, quenching, and cooling steps. Olefin can be removed from the reaction mixture and/or quenched reaction mixture, e.g., by sorption. The removed olefin can be recovered by desorption, e.g., for storage and/or further processing, such as polymerization.

In certain aspects, the catalytic conversion is carried out in at least one reverse-flow reactor. The reverse-flow reactor comprises catalyst, a first thermal mass, and a second thermal mass. When operating the reverse-flow reactor in the forward direction, the first thermal mass, which has been preheated, transfers heat to alkane and oxidant in order to (i) cool the first thermal mass and (ii) heat the alkane and oxidant to a temperature sufficient for catalytically reacting them to produce a first reaction mixture. The first reaction mixture, which comprises $C_{2+}$ hydrocarbon produced by the reaction (e.g., olefin) and any unreacted feed, transfer heat to the second thermal mass to (i) heat the second thermal mass and (ii) cool the first reaction mixture. The flow of alkane and oxidant is then reversed.

When operating the reverse-flow reactor in the reverse direction, the second thermal mass (which is heated when the reactor is operated in the forward direction) transfers heat to alkane and oxidant to (i) cool the second thermal mass and (ii) heat the alkane and oxidant to a temperature sufficient for catalytically reacting them to produce a second reaction mixture. The second reaction mixture, which comprises $C_{2+}$ hydrocarbon produced by the reaction (e.g., olefin) and any unreacted feed, transfers heat to the first thermal mass to (i) heat the first thermal mass and (ii) cool the second reaction mixture. Since the first thermal mass is now heated and the second thermal mass is now cooled, the reverse-flow reactor is substantially restored to its initial condition. The flow of alkane and oxidant can be reversed again, in order to carry out the reaction in the forward direction. The process can be operated continuously or semi-continuously, e.g., by alternating the flow direction of alkane and oxidant to the reverse-flow reactor, such as forward-flow, followed by reverse-flow, flowed by forward flow, followed by reverse-flow, etc.

Optionally, the reverse-flow reactor further comprises sorbent, e.g., at least one sorbent for removing olefin from the first reaction mixture when the process is operated in the forward direction and/or at least one sorbent for removing olefin from the second reaction mixture when the reactor is operated in the reverse direction. Optionally (i) the first thermal mass includes a first sorbent, or is itself, at least in part, a first sorbent and/or (ii) the second thermal mass includes a second sorbent, or is itself, at least in part, a second sorbent. Optionally, a plurality of reverse-flow reactors is utilized for operating the process, the reactors being arranged in series, parallel, or series-parallel.

The process can further comprise, e.g., (i) removing olefin from the first reaction mixture with a second sorbent when the reverse-flow reactor is operated in the forward direction, and then desorbing from the second sorbent at least a portion of the removed olefin and (ii) removing olefin from the second reaction mixture with a first sorbent when the reverse-flow reactor is operated in the reverse direction, and then desorbing from the first sorbent at least a portion of the removed olefin.

The reverse-flow reactor can comprise, e.g., first and second thermal masses, each having first and second portions, the first and second portions together comprising ≥99.0 wt. % of the first or second thermal mass as the case may be, wherein the first and thermal masses each include one or more passages adapted for fluid flow. The reactor can include first, second, third, fourth, and fifth regions, wherein (i) the first and second regions are adjacent, non-overlapping regions, (ii) the third and fourth regions are adjacent, non-overlapping regions, (iii) the first region contains the first portion of the first thermal mass and the second region contains the second portion of the first thermal mass, (iv) the third region contains the first portion of the second thermal mass and the fourth region contains the second portion of the second thermal mass, (v) the fifth region is a non-overlapping region located between the second and third regions, and (vi) the fifth region is adapted for distributing fluid between the first and second thermal masses and optionally for fluid mixing. In order to react alkane and oxidant, e.g., in a forward direction, at least one first reaction zone can be located in the second region, at least one of the reaction zones containing at least one first hydrocarbon conversion catalyst that is in fluid communication with the passage(s) of the first thermal mass. At least one first sorbent zone can be located in the first region, the first sorbent zone containing at least one olefin-selective sorbent that is in fluid communication with the passage(s) of the first thermal mass. In order to react alkane and oxidant in a reverse direction, at least one second reaction zone located in the third region, at least one of the reaction zones containing at least one second hydrocarbon conversion catalyst that is in fluid communication with the passage(s) of the second thermal mass. At least one second sorbent zone can be located in the fourth region, the second sorbent zone containing at least one olefin-selective sorbent that is in fluid communication with the second thermal mass.

In other aspects, the invention relates to one or more flow-through reactors. The reactors are suitable for carrying out the process of any of the preceding aspects. In other aspects, the invention relates to a system for converting alkane to $C_{2+}$ olefin.

Figure 1A:
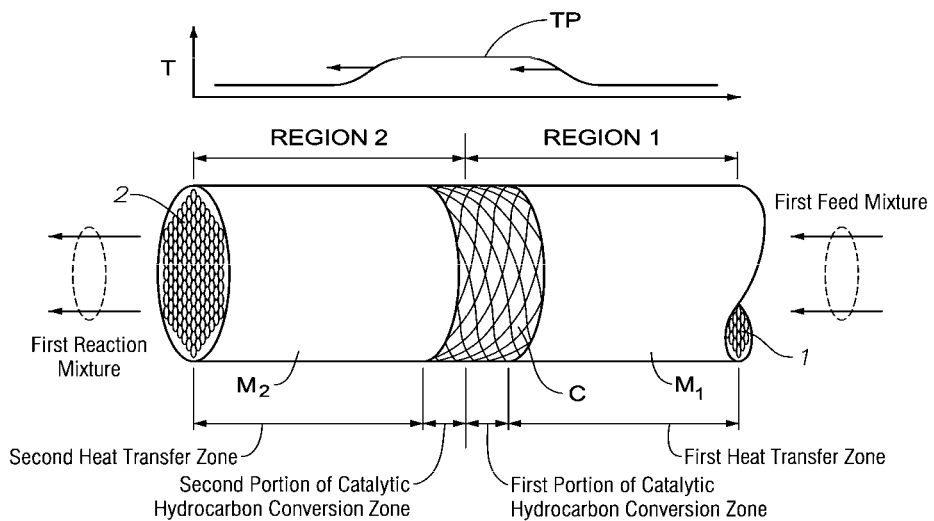
FIGS. 1A and 1B are simplified diagrammatic illustrations of certain process steps in a regenerative reverse-flow reactor system.

Although the invention can be described in terms of a hydrocarbon conversion process, particularly an oxidative-transfer reaction process, for producing olefins such as ethylene and propylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention.

DETAILED DESCRIPTION OF THE INVENTION

Definitions

For the purpose of this description and appended claims, the following terms are defined.

The term "conduit" refers to means for conducting a composition from one location to another. The term conduit encompasses (i) elementary conducting means, such as a pipe or tube and (ii) complex means such as tortuous pathways through conducting means, e.g., pipes, tubes, valves, and reactors that are filled with random packing. One or more conduits are typically utilized for conveying fluid into and through the thermal mass. A single conduit located in a thermal mass is a passage, and the thermal mass typically includes at least one passage. The term "passage" means a geometrically contiguous volume element that can be utilized for conveying a fluid within a reactor, regenerator, recuperator, reactor bed, regenerative bed, thermal mass, monolith, honeycomb, etc. Generally, the thermal mass contains at least one channel (arranged as a physical and/or conceptual set or group of passages). The term "channel" means a plurality of passages that can be utilized together for conveying a fluid within the reactor, regenerator, recuperator, regenerative bed, monolith, honeycomb, etc. For example, a honeycomb monolith can comprise a single channel, the channel having a plurality of passages, e.g., hundreds of thousands of passages per square meter of the honeycomb's cross-section.

The term "sorbent" means a material that removes (e.g., by sorbing and/or or attracting) a substance from another substance. For example, a sorbent is a material which attracts at least one predetermined substance from a mixture comprising the predetermined substance and further comprising at least a second substance. A sorption carried out under "kinetic sorption conditions" is one where sorption is halted before equilibrium sorption conditions are achieved. Kinetic sorption conditions can be obtained, e.g., by operating the sorption at a higher rate per volume of sorbent, by shortening the length of the sorbent bed, etc. The term sorbent includes "absorbent" and "adsorbent." An absorbent is a material that absorbs or incorporates a substance into the body of the absorbent material, which can also be referred to as absorption. For example, an absorbent can be used to absorb or attract or remove or extract a substance from another substance or from a mixture of substances.

The term "$C_n$" hydrocarbon wherein n is a positive integer, e.g., 1, 2, 3, 4, or 5, means hydrocarbon having n carbon atom(s) per molecule. The term "$C_{n+}$" hydrocarbon wherein n is a positive integer, e.g., 1, 2, 3, 4, or 5, means hydrocarbon having at least n carbon atom(s) per molecule. The term "$C_{n-}$" hydrocarbon wherein n is a positive integer, e.g., 1, 2, 3, 4, or 5, means hydrocarbon having no more than n number of carbon atom(s) per molecule. The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The term "alkane" means substantially saturated compounds containing hydrogen and carbon only, e.g., those containing $\leq 1\%$ (molar basis) of unsaturated carbon atoms. The term alkane encompasses $C_1$ to $C_5$ linear, iso, and cyclo alkanes.

The term "$C_n$ unsaturate" means a $C_n$ hydrocarbon containing at least one carbon atom directly bound to another carbon atom by a double or triple bond.

The term "Periodic Table" means the Periodic Chart of the Elements, as it appears on the inside cover of The Merck Index, Twelfth Edition, Merck & Co., Inc., 1996.

The term "oxidant" means any oxygen-bearing material which, under the conditions in the reaction zone, yields an oxygen atom for oxidative coupling and/or oxydehydrogenation. While not wishing to be limited to theory, molecular oxygen atom may be provided as a reactive gas in a gaseous zone and/or atomic oxygen may be provided from a catalyst surface as, for instance in reacted or sorbed forms.

The term "oxidative coupling" refers to the oxygen-assisted dehydrogenation and coupling (formation of C—C bonds) of alkane (particularly methane) to produce water and hydrocarbon of higher order, such as producing $C_2$ hydrocarbon from methane. The term "oxydehydrogenation" means oxygen-assisted dehydrogenation of an alkane, particularly a $C_{2+}$ alkane, to produce an equivalent alkene and water without coupling.

The term "reaction stage" or "reactor stage" means at least one flow-through reactor, optionally including means for conducting one or more feeds thereto and/or one or more products away therefrom.

With respect to flow-through reactors, the term "residence time" means the average time duration for non-reacting (non-converting by oxidative coupling) molecules (such as He, $N_2$, Ar) having a molecular weight in the range of 4 to 40 to traverse the flow-through reactor or a defined zone within the flow-through reactor, such as a reaction zone.

With respect to flow-through reactors, the term "region" means a location within the reactor, e.g., a specific volume within the reactor and/or a specific volume between a flow-through reactor and a second reactor, such as a second flow-through reactor. With respect to flow-through reactors, the term "zone", refers to a specific function being carried out at a location within the flow-through reactor. For example, a "reaction zone" (or "reacting zone" or "reactor zone") is a location within the reactor for conducting a reaction, e.g., a "catalytic hydrocarbon conversion zone" is a location in the rector for carrying out catalytic hydrocarbon conversion, such as catalytic oxidative coupling and/or catalytic oxydehydrogenation. Similarly, a "sorption zone" (or "sorbing zone" or "desorbing zone") is a location within the reactor for sorbing and/or desorbing products of the catalytic hydrocarbon conversion, e.g., $C_{2+}$ hydrocarbon, such as $C_{2+}$ olefin. Similarly, a "quench zone" or "quenching zone" is a location within the reactor for transferring heat from products of the catalytic hydrocarbon conversion, such as $C_{2+}$ olefin.

The term "thermal catalytic oxidative coupling reactor" means an oxidative coupling reactor wherein 50.0% of the heat utilized by the oxidative coupling reaction is provided by heat transfer from at least one thermal mass, e.g., at least one heat storage/heat transfer material associated with the reactor, such as tubulars or bed materials; optionally $\geq 80.0\%$ or $\geq 90.0\%$ of the heat utilized by the oxidative coupling reaction is provided by such heat transfer. Optionally, a net exothermic reaction (e.g., combustion) occurs within the thermal catalytic oxidative coupling reactor, e.g., for preheating and/or reheating the first and/or second thermal masses.

Representative Reactions

In certain aspects, the invention relates to a process for converting reactant and oxidant in the presence of catalyst and at least one thermal mass, the catalyst and thermal mass being located in a flow-through reactor. The flow-through reactor comprises a reactor vessel configured for fluid-flow. The reactor vessel is typically in the form of an elongated vessel having at least two apertures. The first aperture is configured for admitting fluid, e.g., a feed mixture, to the reactor. The second aperture is configured for conducting away from the reactor at least a portion of a reaction mixture produced by catalytically reacting at least a portion of the feed mixture. The reactor vessel can be of any cross-sectional shape, e.g., circular, elliptical, polygonal, etc. For example, the reactor vessel can be an elongated tube having a substantially circular cross section of substantially constant internal diameter, the first and second aperture being located proximate to opposed ends of the elongated tube. The reactor further comprises at least one hydrocarbon conversion catalyst. Typically, substantially all of the hydrocarbon conversion catalyst is located within the reactor vessel. The hydrocarbon conversion catalyst is configured for contact with the fluid-flow, e.g., with the feed mixture. The hydrocarbon conversion catalyst typically includes (i) at least one oxidative coupling catalyst and/or (ii) at least one oxydehydrogenation catalyst. The flow-through reactor vessel can further comprise at least one sorbent. Typically, the sorbent is located downstream of the hydrocarbon conversion catalyst with respect to the fluid-flow. Substantially all of the sorbent can be located in the reactor vessel. The sorbent can be one that is selective for olefin sorption. The sorbent is configured for contact with the fluid-flow, e.g., for contact with the reaction mixture. The flow-through reactor further comprises at least one thermal mass. Typically, substantially all of the thermal mass is located in the reactor vessel. The thermal mass is configured for thermal contact with the fluid-flow. The thermal contact can be direct thermal contact, e.g., with the feed mixture (or one or more components thereof) and/or the reaction mixture (or one or more components thereof). The thermal contact can be indirect thermal contact, such as when heat is transferred between the thermal mass and the fluid-flow through an intermediate material. Typically, the thermal mass is a solid thermal mass having passages for conducting the fluid-flow, with direct heat transfer occurring from the fluid flow to at least part of the thermal mass. Typically, a least a part of the thermal mass is located downstream of the hydrocarbon conversion catalyst with respect to the fluid-flow. For example, at least a portion of the thermal mass can be located in the reactor vessel between the hydrocarbon conversion catalyst and the sorbent. At least a portion of the catalyst and/or thermal mass can be located on (or within) the thermal mass, e.g., on an internal surface of the thermal mass in contact with the fluid-flow. Typically, sorbent and hydrocarbon catalyst are each located within zones of the thermal mass, e.g., a catalysis zone and a sorption (sorbing/desorbing) zone. The zones can be overlapping or non-overlapping. Heat transfer between the fluid-flow and thermal mass is carried out in at least one heat-transfer zone. When the heat transfer includes quenching at least a portion of the reaction mixture, the heat-transfer zone is referred to as a quench zone. When the heat-transfer zone is utilized for transferring heat to a feed mixture or to one or more components thereof, the heat transfer zone is called a pre-heat zone. When the heat-transfer zone is utilized for transferring heat from a feed mixture or from one or more components thereof, the heat transfer zone is called a pre-cool zone.

The flow-through reactor is suitable for carrying out a catalytic hydrocarbon conversion. In certain aspects the invention relates to an alkane conversion process carried out in a catalytic flow-through reactor. The process includes providing a first flow, the first flow comprising alkane and oxidant and having an alkane:oxidant molar ratio ≥2.0. The first flow is introduced into the reactor vessel via the vessel's upstream aperture, and flows into the reactor in an average flow direction, from upstream to downstream. The catalytic flow-through reactor is configured to accept the first flow. The hydrocarbon conversion catalyst has an initial average temperature in the range of 550° C. to 1100° C. At least a first portion of the thermal mass is located downstream of the hydrocarbon conversion catalyst with respect to the first flow's flow direction. The first portion of the thermal mass has an initial average temperature such that [the hydrocarbon conversion catalyst's initial average temperature—the first portion of the thermal mass's initial average temperature] is ≥50° C.

The process further includes catalytic hydrocarbon conversion, which includes transferring hydrogen from the alkane to the oxidant to produce a reaction mixture. The catalytic transfer is carried out in the presence of the hydrocarbon conversion catalyst. The reaction mixture comprises (i) olefin produced by the catalytic transfer and (ii) any unreacted alkane and/or any unreacted oxidant. The reaction mixture is quenched in the flow-through reactor by transferring heat from the reaction mixture to the thermal mass at a location downstream of the hydrocarbon conversion catalyst, downstream being with respect to the first flow's average flow direction. The thermal mass is cooled after the quenching.

The reactor can further comprise sorbent, typically located in the reactor vessel downstream of the hydrocarbon conversion catalyst. Olefin, e.g., $C_{2+}$ olefin, such as ethylene and/or propylene, can be removed from the quenched reaction mixture by contacting the quenched mixture with the sorbent. Alternatively or in addition, conventional methods can be used for separating olefin from the quenched reaction mixture, such as one or more of those disclosed in the Background references cited herein and in the Handbook of Petrochemicals Production Processes, Robert A. Meyers, McGraw Hill, 2005, Chapters 6.1 to 6.3. After sorption, the remainder of the quenched reaction mixture (a raffinate) can be conducted away from the reactor vessel via the downstream aperture. The raffinate typically comprises at least a portion of by-products of the catalytic hydrocarbon conversion, typically one or more of water, molecular hydrogen, carbon dioxide, and carbon monoxide. The raffinate can further comprise any unreacted components of the first flow, e.g., unreacted alkane. Conventional methods can be used for separating unreacted alkane from the raffinate, e.g., for storage and/or further processing, such as recycle to the first flow.

The desired sorbate, typically $C_{2+}$ hydrocarbon such as ethane and/or ethylene, can be recovered (e.g., desorbed) from the sorbent by one or more of (i) lessening the average total pressure proximate to the sorbent, (ii) heating the sorbent, and (iii) flowing a utility fluid proximate to the sorbent. For example, the first flow can be lessened or substantially halted, and a utility fluid introduced into the reactor vessel's first aperture flowing in the same average flow direction as the first flow. Heat is transferred to the utility fluid from the hydrocarbon conversion catalyst, resulting in a cooled hydrocarbon conversion catalyst and a heated utility fluid. Heat is transferred from the heated utility fluid to the sorbent downstream of the hydrocarbon conversion catalyst, resulting in (a) a heated sorbent, (b) a cooled utility fluid, and (c) desorption of at least a portion of the sorbed olefin. The cooled utility fluid conveys the desorbed olefin away from the reactor vessel via the vessel's second aperture. Conventional methods can be used for separating the desired sorbate from the cooled utility fluid. Further separations can be carried out if needed. For example, when the desired sorbate includes ethane and ethylene, as may be the case when the sorbent is selective for hydrocarbon sorption but less-selective for olefin sorption, further separations can be carried out for separating ethylene from ethane.

The process can be operated continuously or semi-continuously. For example, in certain aspects, the flow-through reactor is substantially adiabatic and comprises a catalytic hydrocarbon conversion zone and a quench zone, with the catalytic hydrocarbon conversion being net exothermic. Since flow-through reactor is substantially adiabatic and the catalytic hydrocarbon conversion reaction is net exothermic, feed mixture flow is lessened or substantially halted before that portion of the thermal mass in the quench zone (e.g., the first portion of the thermal mass) has an average temperature that is substantially the same as or exceeds that of the reaction mixture entering the quench zone (at which point the reaction mixture would not be quenched). After feed mixture flow is curtailed or substantially halted, the catalytic hydrocarbon conversion zone and quench zone can be restored to operating temperature, e.g., to an average temperature of the catalytic hydrocarbon conversion zone in the range of 550° C. to 1100° C. and an average temperature in the quench zone such that [the hydrocarbon conversion catalyst's average temperature—the first portion of the thermal mass's average temperature] is ≥50° C. This can be carried out by transferring heat away from the catalytic hydrocarbon conversion zone and the quench zone, e.g., by transferring heat away from the catalytic hydrocarbon conversion catalyst and/or the thermal mass, such as from the first portion of the thermal mass. To do this, a flow of cool utility fluid (e.g., at ambient temperature) is introduced into the first aperture of the flow-through reactor. The temperature of the cool utility fluid is selected such that heat transfer to the utility fluid from the heated hydrocarbon conversion catalyst results in (i) an average temperature of the hydrocarbon conversion catalyst in the range of from 550° C. to 1100° C. and (ii) a moderated utility fluid having a temperature less than that of the heated quench zone. Heat is then transferred in the quench zone from the heated first portion of thermal mass (heated as a result of the reaction mixture quenching) to the moderated utility fluid to produce a heated utility fluid and a cooled first portion of the thermal mass. The cooled quench zone typically has an average temperature that is the same as or warmer than the cooled catalytic hydrocarbon conversion zone. Additional cooling is utilized to restore the quench zone to an average temperature such that [the hydrocarbon conversion catalyst's average temperature—the first portion of the thermal mass's average temperature] is ≥50° C., e.g., by additional heat transfer away from the thermal mass. Utility flow is now lessened or substantially halted, and the flow of feed mixture is re-initiated to continue catalytic hydrocarbon conversion. The process is operated continuously by periodically catalytic the hydrocarbon conversion and the reactor regeneration steps, one after the other.

Representative fluids conducted into, though, and away from the flow-through reactor will now be described in more detail. The invention is not limited to the use and/or production of these fluids, and this description is not meant to foreclose the use/production of other fluids within the broader scope of the invention.

Feeds for the Catalytic Hydrocarbon Conversion

The hydrocarbon conversion process can be carried out by catalytically converting a hydrocarbon-containing reactant (e.g., a hydrocarbon reactant, such as alkane) in the presence of oxidant, e.g., molecular oxygen. The hydrocarbon reactant and oxidant can be components of a feed mixture. The feed mixture can be produced by (i) combining hydrocarbon reactant and oxidant in the flow-through reactor, combining hydrocarbon reactant and oxidant upstream of the flow-through reactor, or a combination thereof. The feed mixture can have a hydrocarbon reactant: molecular oxygen molar ratio ≥2, e.g., ≥4, such as in the range of 2 to 50, or 4 to 20.

The feed mixture is generally at least 10% (weight basis, based on the weight of the feed mixture) of the total feed to the catalytic hydrocarbon conversion (the "total feed).

The remainder of the total feed total feed can be diluent. Typically, the total feed to the reactor comprises ≥20% feed mixture, or ≥30%, or ≥40%. Although the total feed can consist of feed mixture, or consist essentially of feed mixture, the total feed can optionally comprise ≤98% feed mixture, e.g., ≤90%, such as ≤80%, or ≤70%, with the remainder of the total feed comprising diluent. In certain aspects, the hydrocarbon reactant comprises ≥90% alkane (molar basis, per mole of hydrocarbon reactant), e.g., ≥99%, and the total feed has an alkane: oxidant molar ratio in the range of 2 to 50, e.g., 4 to 20. For example, (i) the hydrocarbon reactant can comprise ≥90% methane (molar basis), e.g., ≥99%; the oxidant can comprise ≥90% $O_2$ (molar basis), e.g., ≥99%; and (iii) the total feed can have a methane:$O_2$ molar ratio in the range of 2 to 50, e.g., 4 to 20.

Diluent typically comprises at least one substantially inert (e.g., unreactive) fluid, such as one or more of molecular nitrogen, water, carbon dioxide, helium, argon, etc. Optionally, the total feed comprises diluent in the range of from 5% (weight basis, based on the weight of the total feed) to 90%, or from 10% to 50%. Any convenient method or system can be used for adding diluent to the total feed, or one or more components of the total feed. For example, at least a portion of the total feed's diluent can be added to one or more of (i) the hydrocarbon reactant (e.g., to the alkane component), (ii) the oxidant, (iii) the feed mixture, and (iv) the total feed. Conventional equipment can be utilized for adding diluent to the total feed or one or more components thereof, e.g., by way of one or more steam spargers when the diluent includes steam, but the invention is not limited thereto.

The hydrocarbon reactant can comprise alkane, e.g., one or more of $C_{5-}$ linear, $C_{5-}$ iso, and $C_{5-}$ cyclo alkane. Generally, the hydrocarbon reactant comprises one or more of methane, ethane, propane, butane and pentane. Particular examples include methane, ethane and propane, with methane being a preferred alkane. The hydrocarbon reactant typically comprises ≥10% (molar basis, per mole of hydrocarbon reactant) alkane, e.g., ≥25%, such as ≥50%, or ≥75%, or ≥90%, or ≥99%. For example, the hydrocarbon reactant can consist of alkane, or consist essentially of alkane. In certain aspects, the alkane comprises ≥75% methane, or ≥90%, or ≥99%. In other aspects, the alkane comprises ethane and/or propane, e.g., ≥75% ethane and/or propane, or ≥90%, or ≥99%. In other aspects, the alkane comprises a mixture of methane, ethane, and propane, e.g., a mixture comprising ≥25% methane, ≥5% ethane, and ≥1% propane, such as 25% to 94% methane, 5% to 50% ethane, and 1% to 50% propane. In certain aspects, (i) the alkane comprises methane and (ii) the feed mixture has a methane:oxidant molar ratio in the range of from 2 to 50, or about 4 to 20.

The oxidant typically comprises one or more fluids which yield oxygen under the specified hydrocarbon conversion conditions. Typically, the oxidant includes one or more of molecular oxygen ($O_2$), $O_2^-$, $O_2^=$, ionized oxygen atoms, nitrogen oxides such as $N_2O$, etc. Oxidant is typically in the vapor phase at the specified hydrocarbon conversion conditions, but this is not required, and in certain aspects liquid and/or solid oxidant can be used. The oxidant can comprise $O_2$, e.g., ≥90% $O_2$ (molar basis, per mole of oxidant), such as, ≥99%. For example, the oxidant can comprise $O_2$ in air, or $O_2$ obtained or derived from air, e.g., by separation. The oxidant can comprise (or consist essentially of, or consist of) air. When the oxidant comprises $O_2$ in air, the total feed generally comprises at least a portion of the air's molecular nitrogen as diluent. In other words, when the oxidant comprises molecular oxygen in air, other gasses in the air, such as molecular nitrogen, are considered to be diluent, and are not considered to be part of the oxidant.

The total feed can optionally comprise (i) ≥10% alkane (weight basis based on the weight of the total feed), e.g., ≥25%, or ≥50%, or ≥75%, or ≥90%, or ≥95%, or ≥98% of the total feed; and/or (ii) ≤90%, or ≤80%, or ≤70% of the total feed. The oxidizing component of the first mixture, e.g., oxidant, can comprise at least 2 wt. % of the total feed provided to the reactor, based on total weight of the feed provided to the reactor. The total feed can optionally comprise (i) ≥5% oxidant (weight basis, based on the weight of the total feed), or ≥10%, or ≥20% of the total feed or (ii) ≤90%, or ≤80%, or ≤60%, or ≤40%. In certain aspects, total feed comprises ≥10% alkane and ≥2% oxidant (both percents based on the total feed's weight).

Hydrocarbon Conversion Catalyst

The catalytic hydrocarbon conversion utilizes at least one hydrocarbon conversion catalyst. Any hydrocarbon conversion catalyst capable of carrying out the specified catalytic conversion of the specified hydrocarbon reactant and specified oxidant can be used.

Particularly useful hydrocarbon conversion catalysts include oxydehydrogenation catalysts and oxidative coupling catalysts, such as metal oxide hydrocarbon conversion catalysts useful in oxydehydrogenation and oxidative coupling reactions. The metal oxide catalysts also include mixed metal oxide catalysts, meaning that there may be more than one metal element in the oxide catalyst. Particularly useful metal oxide catalysts are metal oxide catalysts effective in catalytically converting alkane (e.g., methane) to $C_{2+}$ olefin (e.g., ethylene).

Suitable metal oxide catalysts include those which comprise at least one base metal of IUPAC Group 2, Group 3, Group 7, Group 8, Group 9, Group 14, Group 15 and the lanthanide series of metals of the Periodic Table. Examples of Group 1 metals include Li, Na, K, Rb, Cs and Fr. Li, Na, K, Rb and Cs represent more common Group 1 metals. Examples of Group 2 metals include Be, Mg, Ca, Sr, Ba and Ra. Mg, Ca, Sr and Ba are more common Group 2 metals. Examples of Group 3 metals include Sc, Y, La and Ac. La is an example of a particularly common Group 3 metal. Examples of Group 7 metals include Mn and Re. Mn is an example of a particularly common Group 7 metal. Examples of Group 8 metals include Fe, Ru and Os. Fe is an example of particularly common Group 8 metal. Examples of Group 9 metals include Co, Rh and Ir. Co is an example of a particularly common Group 9 metal. Examples of Group 14 metals include Sn and Pb. Pb is an example of a particularly common Group 14 metal. An example of a Group 15 metal includes Bi. Examples of the lanthanide series of metals include Ce, Pr, Nd, Sm, Eu, Gd, Tb, Dy, Ho, Er, Tm, Yb and Lu. Sm, Gd, Ho, and Yb are more common lanthanide metals.

Suitable hydrocarbon conversion catalysts, including those that can be used for oxidative coupling, are disclosed in U.S. Pat. No. 6,096,934, which is incorporated by reference herein in its entirety. Such catalysts include lithium supported on magnesium oxide where the lithium is present in either the hydroxide or oxide form; bismuth supported on calcium oxide where the bismuth is present in either the hydroxide or oxide form; lithium supported on calcium oxide where the lithium is present in either the hydroxide or oxide form; cerium supported on magnesium oxide where the cerium is present in either the hydroxide or oxide form; nickel and lanthanum supported on magnesium oxide where the lanthanum is present in either the hydroxide or oxide form and the nickel is present in the metallic form; and lithium supported on lanthanum oxide where the lithium is present in either the hydroxide or oxide form; or any other metal or metal oxide or hydroxide catalyst promoted with a Group 1, 2, or lanthanide series element present in an oxide or hydroxide form.

Other suitable hydrocarbon conversion catalysts are disclosed in U.S. Pat. No. 5,245,124, and in Y. A. Amenomiya et al. in "Conversion of Methane by Oxidative Coupling," report to CANMET, Energy, Mines and Resources, Ottawa, Canada, both being incorporated by reference herein in their entirety. In order of preference, suitable hydrocarbon conversion catalysts of these references include $Li/Sm_2O_3 > Na/CaO > K/CaO > LaAl_2O_3 > Sm_2O_3 > Li/CaO > PbO > Bi_2O_3 > Ho_2O_3 > Gd_2O_3 > Li/MgO > Li/CaO \sim Yb_2O_3 > Y_2O_3Na/MgO \sim CaO > MgO$. Additives to the catalysts include Ba, Li, Sr, Pb, K, Mg, Ca, Na, and Sb.

Perovskites are also useful for the specified catalytic hydrocarbon conversion of the specified hydrocarbon reactant and specified oxidant. Suitable perovskites include those having the formula $A_2B_2C_3O_{10}$, where A is alkali metal; B is lanthanum or a lanthanide element, for example, cerium, neodymium, samarium, praseodymium, gadolinium or dysprosium; and C is titanium. A particular example is disclosed in U.S. Pat. No. 5,026,945, which is incorporated by reference herein in its entirety. The disclosed perovskites include those having the formula $A_xLn_yTi_zO_{10}$, wherein A is one or more alkali metal; Ln is one or more of lanthanum, cerium, neodymium, samarium, praseodymium, gadolinium and dysprosium; x is about 2; y is about 2; and z is about 3.

One or more of the hydrocarbon conversion catalysts can be incorporated in the specified flow-through reactor, e.g., in a configuration in which the hydrocarbon reactant and oxidant to catalytically react with one another as the hydrocarbon reactant and oxidant transit the flow-through reactor. For example, the hydrocarbon conversion catalyst (and/or one or more components thereof) can be arranged in at least one catalyst bed. The catalyst bed can be located within the flow-through reactor and configured so that one or more of the bed surfaces is exposed to hydrocarbon reactant and/or oxidant transiting the flow-through reactor. Alternatively, or in addition, the hydrocarbon conversion catalyst can be located proximate to one or more thermal mass, e.g., by incorporating at least a portion of the hydrocarbon conversion catalyst in and/or on a thermal mass, e.g., as a coating. For example, the hydrocarbon conversion catalyst (and/or components thereof) can be arranged at one or more surfaces of at least one thermal mass over which the feed components pass, e.g., proximate to that portion of the thermal mass's surface area exposed to hydrocarbon reactant and/or oxidant, such as the thermal mass's interior surface area, including the surface area of the thermal mass's internal passages or channels.

Catalytic Hydrocarbon Conversion

Main conversion reactions in the reaction zone section of the reactor, when the feed to the reactor is comprised of methane and oxygen, are the exothermic reactions to $C_2$ products:

$$CH_4 + \tfrac{1}{4}O_2 \rightarrow \tfrac{1}{2}C_2H_6 + \tfrac{1}{2}H_2O \quad (1)$$

$\Delta H = -87$ kJ/mol $$CH_4 + \tfrac{1}{2}O_2 \rightarrow \tfrac{1}{2}C_2H_4 + H_2O \quad (2)$$

$\Delta H = -192$ kJ/mol and optionally combustion, which consumes more oxygen and generates more heat:

$$CH_4 + 1\tfrac{1}{2}O_2 \rightarrow CO + 2H_2O \quad (3)$$

$\Delta H = -519$ kJ/mol $$CH_4 + 2O_2 \rightarrow CO_2 + 2H_2O \quad (4)$$

$\Delta H = -802$ kJ/mol

It has been found that by regulating the relative amount of reactant and oxidant to the relative amounts specified for the feed mixture, reaction (1) and preferably reaction (2) can be favored over reactions (3) and (4), and over reactions which combust one or more of the desired products. Such undesirable combustion reactions include $C_2H_x + O_2 \rightarrow CO_2 + H_2O$, such as $C_2H_4 + 3O_2 \rightarrow 2CO_2 + 2H_2O$ (-1412 kJ/mol) and $C_2H_6 + 7/2O_2 \rightarrow 2CO_2 + 3H_2O$ (-1517 kJ/mol).

Accordingly, the catalytic hydrocarbon conversion process, e.g., the oxidative coupling of $C_1$ hydrocarbon and/or the oxydehydrogenation of $C_{2+}$ hydrocarbon, can be carried out in one or more of the specified flow-through reactors in the presence of one or more of the specified hydrocarbon conversion catalysts at the specified temperatures and pressures. For example, the catalytic hydrocarbon conversion process is particularly efficient when carried out at reaction zone temperatures of from 550° C. to 1100° C. Alternatively, the hydrocarbon conversion process is particularly efficient at reaction zone temperatures of from 650° C. to 900° C., or at temperatures of from 675° C. to 825° C.

Operating pressures may include a pressure of at least atmospheric pressure (zero pressure, gauge), such as ≥4 pounds per square inch gauge (psig) (28 kilo Pascals gauge (kPag)), or ≥15 psig (103 kPag), or ≥36 psig (248 kPag), or ≥44 psig (303 kPag), or ≥103 psig (700 kPag), but may be ≤300 psig (2064 kPag), or ≤163 psig (1121 kPag), or ≤150 psig (1032 kPag).

Residence time in the flow-through reactor, e.g., in the catalytic hydrocarbon reaction zone of the flow-through reactor is typically ≤20 seconds, e.g., ≤10 seconds, such as ≤5 seconds, or in the range of 0.01 seconds to 20 seconds, or in the range of from 0.5 seconds to 10 seconds. Also, as may be appreciated, these different pressures and temperatures may be utilized together to form different combinations depending on the specific configuration of equipment.

Thermal Mass

The flow-through reactor includes at least one thermal mass. For example, at least a portion of the thermal mass configured so that the it is in thermal contact (direct or indirect) with the reaction mixture produced by the specified catalytic hydrocarbon conversion, and optionally in thermal contact (direct or indirect) with at least one component of the total feed, e.g., at least one of the hydrocarbon reactant, the oxidant, and the diluent. The thermal mass is selected from among materials which are capable of transferring heat to and/or from (i) the specified feed mixture or one or more components thereof and (ii) storing heat. At least a portion of the thermal mass is located within the flow-through reactor in a quench zone of the flow-through reactor that is located downstream (with respect to average flow of the specified reaction mixture) of the flow through reactor's catalytic hydrocarbon conversion zone.

Generally, at least a portion of the thermal mass is located within the flow-through reactor for quenching the specified reaction mixture, typically in at least one quench zone. Besides the quench zone, a thermal mass or portion thereof can be located in the flow-through reactor proximate to one or more of the catalytic hydrocarbon conversion zone, the quench zone, and the sorption zone. When the thermal mass encompasses more than one zone (more than one of a catalytic zone, a quench zone, and a sorbent zone), there need not be any physical manifestation within the thermal mass of the zone's beginning or end. It may simply be a mathematical construct defining an area or volume within an otherwise homogenous thermal mass.

The thermal mass can be of substantially any form or shape, such as, but not limited at least one of spheres, beads, honeycomb materials, a tube, pipe, U-tube, fluid mixer, nozzle, extruded monolith, brick, tile, catalyst tray, reactor tray, tray component, valves, and/or other refractory components that are exposed to high temperature. The thermal mass can be segmented, with each segment having a first end (e.g., a beginning) and a second end (e.g., an ending). Each end is represented by a cross sectional area that is approximately orthogonal to average (or net) flow direction, e.g., the first end corresponds to the upstream end and the second end corresponds to the downstream end of the thermal mass or thermal mass segment. The thermal mass or portion thereof can be in monolith form. When a thermal mass includes a plurality of monoliths, the individual monoliths can be arranged in parallel, series and/or series parallel. Suitable monoliths include those formed by extruding or die pressing ceramic into particular shapes, e.g., polygonal shapes, such as shapes having regular polygonal cross-section, such as triangular, rectangular, hexagonal, star, etc. cross-section. Shaped monoliths can be stacked, e.g., into two- or three-dimensionally stacks, such as blocks above, behind, and beside each other. Monoliths are particularly effective as thermal mass because they provide high heat transfer capacity with lessened pressure drop. The shape of the thermal mass is not restricted to any particular geometry. For example, the thermal mass can be elongated, and can have elliptical, cylindrical, and/or rectangular cross-sections, including combinations thereof. A plurality of thermal masses can be of the same shape and size, but this is not required. A thermal mass can be in the form of one or more honeycomb monoliths of substantially cylindrical cross-section. Thermal mass channels can comprise a plurality of passages (e.g., those in a conceptual or physical "pie-slice" of the monolith's cross-sectional area. The passages of each channel typically comprise substantially parallel, substantially independent flow-paths within the honeycomb. The passages within the reacting, quenching, and or sorbing zones of a thermal mass can each be of the same size and shape.

In certain aspects, one or more of the thermal masses includes separate passages through reactor components to manage the flow of one or more components of the reaction mixture and/or the feed mixture through the thermal mass. The passages and/or channels can be separate, e.g., passages that comprise flow barriers that effectively function as walls to lessen or prevent cross flow or mixing of fluids (e.g., reactants and/or products) between passages, except in the desired regions of the reactor. Suitable thermal masses include those having a plurality of passages, which are typically configured for parallel-flow, e.g., channeled thermal masses comprising one or more honeycomb monoliths. Typical honeycomb monoliths include a plurality of parallel channels, each channel comprising a plurality of passages, the passages being arranged in parallel fashion with walls serving to separate each passage.

Typically, one or more thermal mass is configured proximate to at least one catalyst bed used for carrying out the specified catalytic hydrocarbon conversion. For example, the thermal mass can comprise one or more multi-functional, refractory honeycomb, e.g., one having at least (i) sorbent functionality, (ii) heat transfer/heat storage functionality, and (iii) catalytic functionality for one or more of the specified catalytic hydrocarbon conversion reactions. Optionally, at least a portion of the sorbent functionality is located in or proximate to one or more of the passages through the honeycomb, in fluidic-contact with the specified reaction mixture. Optionally, at least a portion of the catalytic functionality is located in or proximate to one or more of the passages through the honeycomb, in fluidic-contact with one or more of the specified feed mixture (or one or more components thereof), and/or the specified reaction mixture (or one or more components thereof). The catalytic functionality of the refractory monolith is typically located downstream of the flow-through reactor's inlet aperture, with downstream being with respect to the average flow of feed mixture, At least a portion of the thermal mass functionality is typically located downstream of the catalytic functionality. The sorbent functionality can be co-located with the thermal mass functionality, but this is not required, and in certain aspects at least a portion of the sorbent functionality is located downstream of the thermal mass functionality.

When a segmented thermal mass is used, one or more mixer/distributor means can be used between thermal mass segments, e.g., to improve the oxidative coupling reaction. Mixer mechanisms, distributor mechanisms, reactor system internals, flow-control mechanisms, etc., for the reactor can be substantially the same as those described in U.S. Pat. No. 7,943,808 and/or U.S. Patent Application Publication No. 2013/157205, for example.

The thermal mass can include material typically used in fabrication of at least one of a honeycomb monolith, a reactor bed, a reactor conduit, a reactant mixer, a reactant distributor, and a reactant mixer/distributor. Thermal mass can be selected from any material which can maintain integrity, functionality, and withstand long term exposure to the relevant temperatures for the oxidative coupling and combustion reactions. Non-limiting examples of such materials include one or more of glass or ceramic beads or spheres, metal beads or spheres, ceramics, ceramic or metal honeycomb materials, ceramic tubes, extruded monoliths, and the like. In particular aspects, the thermal mass is capable of absorbing and storing heat and releasing the stored heat, without any significant phase change, over a temperature range in which the specified catalytic hydrocarbon conversion (and optional hydrocarbon combustion) are carried out. Examples of temperature ranges at which the thermal mass absorbs, stores and releases heat include a range of from 50° C. to 1500° C., alternatively from 100° C. to 1500° C. or from 200° C. to 1500° C.

The thermal mass and the materials from which thermal mass is made and/or includes can be characterized by one or more properties.

Melting temperatures (melting points) are reflective of the ability of the thermal mass to withstand combustion and oxidative coupling temperatures without chemical change and/or physical destruction. Thermal masses having higher melting points are preferred according to this invention. For example, the melting point (or decomposition temperature) of the thermal mass of this invention is preferably at least 1200° C., or at least 1500° C., measured at atmospheric pressure.

Porosity is a measure of the effective open pore space in the thermal mass into which heat and gasses can penetrate and eventually degrade the structure. The porosity of a thermal mass can be expressed as the average percentage of open pore space in the overall refractory volume. As an example, the thermal masses utilized in certain aspects of the invention can have a porosity of not greater than 50%, or not greater than 40%, or not greater than 30%. The porosity can be measured by an Archimedes process, e.g., mercury porosimitry.

Bulk density is a measure of the weight of a given volume of the thermal mass. Higher bulk densities, with lower porosities, can be particularly effective. As an example, the thermal masses can have a bulk density of at least 0.5 g/cm$^3$. For example, the bulk density can be from 0.5 g/cm$^3$ to 3.5 g/cm$^3$ or from 1 g/cm$^3$ to 3 g/cm$^3$.

Thermal conductivity is defined as the quantity of heat that will flow through a unit area in direction normal to the surface area in a defined time with a known temperature gradient under steady state conditions. Thermal conductivity represents a general heat flow characteristic of the thermal mass. Higher thermal conductivity thermal masses are preferred. For example, the thermal mass can have a thermal conductivity of from 0.1 W/mK to 50 W/mK or from 0.2 W/mK to 30 W/mK.

Thermal expansion of the thermal mass should not be so great such that cracking of the material occurs during operation of the reaction system. In one aspect, the thermal mass can be characterized by a thermal expansion coefficient. For example, the thermal mass can have a thermal expansion coefficient of from $0.1 \times 10^{-6}$/K to $20 \times 10^{-6}$/K or from $0.2 \times 10^{-6}$/K to $15 \times 10^{-6}$/K. In this example, the thermal expansion coefficient is given as a value in a temperature range of from 25° C. to 800° C.

Thermal capacity is the ability of a material to hold heat. The thermal masses can have a higher thermal capacity, but not so high as to increase the probability of cracking at higher temperatures. For example, the thermal masses utilized in certain can have a thermal capacity of from 250 Jm$^3$/K to 4500 Jm$^3$/K or from 500 Jm$^3$/K to 3000 Jm$^3$/K.

For thermal mass located in or proximate to a sorbent zone, the thermal mass itself can have sorbing functionality. For example, certain ceramics can act as a sorbent, while also functioning to adsorb and/or release heat. Thus, the thermal mass can be one material that is bi-functional.

The thermal mass or portion thereof can be in the form of bedding and/or packing material, e.g., one or more of beads or spheres; monoliths (e.g., extruded honeycomb and/or tubes), catalysts; checker bricks, and tiles. Suitable thermal masses include those comprising ceramic, e.g., one or more yttria, zirconia, alumina, silica, and other refractory material capable of adsorbing, storing and transferring heat, and that are effective in withstanding temperatures within the oxidative coupling reactor. The ceramic can be vitreous or non-vitreous, but is typically non-vitreous.

At each step of the process, a specified zone has a characteristic "average zone temperature" that is an average over all locations in the zone, from the beginning of the zone to the end of the zone, and over a specified period of time. For example, the average zone temperature of a reaction zone during catalytic hydrocarbon conversion can be determined as an average temperature from the beginning of the reaction zone to the end, which is determined over the time period reactants are catalytically reacting the zone. To compare average zone temperatures, such as the average zone temperature of a reaction zone to (i) a sorption zone during sorption or (ii) a heat transfer zone during heat transfer, the average temperature from the beginning of a zone to the end of a zone are preferably determined over comparable time periods in which fluids flow through the respective zones. Although the thermal mass can be in thermal equilibrium at a substantially constant temperature over all its locations, this is not required, and in certain aspects a thermal mass exhibits temperature profile indicating a progression or decrease in temperature across the thermal mass. This can be the case when there is heat exchange between fluid flowing through the thermal mass and the thermal mass itself.

Thermal mass characteristics and configurations can be characterized in terms of tortuosity ($\tau$), void fraction ($\epsilon$) and wetted area ($a_v$). Within any zone, the thermal mass can have a constant or non-constant $a_v$. If the zone is homogenous in contents, $a_v$ will be constant throughout the zone. If the zone is inhomogeneous, then $a_v$ should be taken as a volume average over the zone.

Tortuosity tends to impact the momentum transfer rate more than the heat transfer rate, so low tortuosity packing is typically utilized (e.g., straight-channel honeycombs, such as one or more channels having a plurality of parallel passages). Void fraction determines the ratio of heat-storing solids in the bed relative to the fluid-carrying passages, and it can be adjusted over a wide range without impacting the heat transfer rate or momentum transfer rate. Wetted area directly relates to certain heat transfer properties, such as convective heat transfer and conductive heat transfer, while also directly relates to the momentum transfer rate. The impact of wetted area is similar for convective heat transfer and momentum transfer rate. Thus, for flow-through reactors employing convective heat transfer, the selection of wetted area provides a design tradeoff between high heat transfer (efficiency and selectivity) versus high momentum transfer, which manifests as pressure drop, e.g., resulting in reactor design difficulties.

A specific wetted area can be used in a specific zone of the flow-through reactor, e.g., in a specific zone of the thermal mass. The specific wetted area is selected based on the dominant heat transfer mode at the specified zone, e.g., via radiation, convection, conduction, or some combination thereof. For example, a first portion of a thermal mass, e.g., a portion located in a catalytic hydrocarbon conversion zone, can include passages having a wetted area $a_{v1}$, while a second portion of the thermal mass, e.g., a portion located in a quenching zone, can include passages having a second wetted area $a_{v2}$. The wetted areas $a_{v1}$ and $a_{v2}$ can be different (e.g., $a_{v1} \neq a_{v2}$) and may include wetter areas $a_{v1}$ and $a_{v2}$ being different from each other by at least 25%, at least 30%, at least 40% or at least 50%.

The thermal mass may include (i) a first channel (e.g., for hydrocarbon reactant) comprising a first plurality passages and having a first wetted area $a_{v1}$; and (ii) a second channel (e.g., for oxidant) comprising a second plurality of passages and having a second wetted area $a_{v2}$, wherein (i) $a_{v1} \neq a_{v2}$ and (ii) $a_{v2}$ is different from $a_{v1}$ by at least 25%. The difference percentage for $a_v$, as used herein, is defined to be based on the higher of the two wetted areas. For example, if $a_{v1} \geq a_{v2}$, then the percent difference between $a_{v1}$ and $a_{v2}$ is $100*(a_{v1}-a_{v2})/a_{v1}$.

Sorbents

The flow-through reactor optionally comprises sorbent, e.g., sorbent located in a sorbent zone within the flow-through reactor. Sorbent, when used, can be configured to selectively remove or extract hydrocarbon from other components of the reaction mixture produced by the specified catalytic hydrocarbon conversion. For example, the sorbent can be selected from among those that are selecting for removing from the reaction mixture one or more of $C_{2+}$ hydrocarbon, e.g., $C_{2+}$ unsaturates, such as $C_{2+}$ olefin, particularly ethylene and/or propylene. The sorbent can be located within the flow-through reactor, e.g., at a location downstream of the thermal mass, but this is not required. In certain aspects, the sorbent is located within the flow-through reactor proximate to at least a portion of the thermal mass, e.g., in or on at least a portion of the thermal mass, such as in or on that portion of the thermal mass that is located in the flow-through reactor's quench zone. In other words, the sorption zone and quench zones of can be overlapping zones of the flow-through reactor.

When used, sorbent can be located in a sorption zone of the flow-through reactor that is downstream of the catalytic hydrocarbon conversion zone. A quench zone, comprising thermal mass can located between the catalytic hydrocarbon conversion zone and the quench zone. During sorption, the average zone temperature in the sorption zone is typically at an average zone temperature that is lower than that of the average zone temperature within the catalytic hydrocarbon conversion zone. As an example, the sorption zone (during sorption) can be at an average zone temperature of at least 50° C., or at least 100° C., or at least 200° C. lower than the average zone temperature within the catalytic hydrocarbon conversion zone. Although sorption can be carried out in equilibrium, the flow-through reactor is typically operated under kinetic sorption conditions, particularly when the flow-through reactor is a reverse-flow reactor.

In a case in which the sorbate includes at least one of ethylene and propylene, sorption can be carried out at a temperature $\geq 150°$ C., e.g., $\geq 200°$ C., or $\geq 250°$ C., such as in a range of from 50° C. to 500° C., or 200° C. to 475° C. Alternatively, in a case in which the sorbate includes at least one of ethylene and propylene, sorption can be carried out at a temperature range of from 100° C. to 400° C., or from 150° C. to 350° C., or from 200° C. to 300° C.

Pressure at which sorption is carried out is typically within the pressure range of the reaction zone. As a practical matter, the pressure can be less than that of the reaction zone, since the sorption zone is generally downstream of the reaction zone and some pressure drop will naturally occur due to typical physical constrains within the reactor.

Suitable sorbents include high surface area, porous materials which have been treated with metal species capable of π-complexation with olefins, such as copper and silver salts. Such sorbents are described in U.S. Pat. No. 4,917,711, which describes the use of supports such as zeolite 4A, zeolite X, zeolite Y, alumina and silica, each treated with a copper salt, to selectively remove carbon monoxide and/or olefins from a gaseous mixture containing saturated hydrocarbons (i.e. paraffins) such as ethane and propane.

Suitable sorbents include those which comprise copper salts and silver compounds supported on one or more of silica, alumina, MCM-41 zeolite, 4A zeolite, carbon molecular sieves, polymers such as Amerberlyst-35 resin, and alumina.

Suitable clay-based sorbents, including $Ag^+$ impregnated clay sorbents, are disclosed in U.S. Pat. Nos. 6,867,166 and 6,423,881, which are incorporated by reference herein in their entirety, and in Choudary et al., *Ind. Eng. Chem. Res.* 2002, v 41, p. 2728, which is also incorporated by reference herein in its entirety. Other useful sorbents are described in U.S. Pat. Nos. 4,717,398; 6,200,366; and 5,365,011, and in Van Miltenburg et al., *Chemical Engineering Research and Design,* 2006, 84(A5) p. 350, all of which are incorporated by reference herein in their entirety. These references disclose modified Faujasite zeolites, which are used for the separation of ethylene from ethylene/ethane mixtures. Suitable sorbents can be selected from among aluminophosphates, such as described in U.S. Pat. No. 6,293,999, which is incorporated by reference herein in its entirety. Analogous zeolite sorbents can also be used. Particularly suitable sorbents include one or more metal-organic frameworks which are capable of selectively separating olefin (e.g., $C_{3-}$ olefin) from fluid mixtures (such as $C_{4-}$ hydrocarbon mixtures), e.g., one or more of which having at least one Fe-organic framework. Suitable metal-organic frameworks having a redox-active metal center (e.g., Fe2(dobdc)), are disclosed in U.S. Patent Publication No. 2013/0053585, which is incorporated by reference herein in its entirety.

Following sorption of the desired sorbate, raffinate is conducted away from the sorbtion zone. The raffinate is lean of the sorbate, and typically comprises an amount of the desired sorbate that is ≤0.5 times the amount of the desired sorbate in the reaction mixture. The appearance of an increased amount of the desired sorbate in the raffinate (called "break-through") is an indication that the sorbent is approaching its ultimate capacity. Within a predetermined time before, at, or after break-through, the passing of the reaction mixture to the sorbent can be lessened or discontinued, in order to desorb sorbate from the sorbent.

When the sorbent is one that is selective for sorbing $C_2$ hydrocarbon from the reaction mixture, desorption is carried out in order to (i) regenerate the one $C_2$-selective sorbent (to restore capacity for sorbing the reaction mixture's $C_2$ composition) and (ii) to recover the desorbed $C_2$ composition. Conventional sorbent regeneration conditions are suitable. Desorption be carried out by a reduction in temperature, pressure or both.

The sorption zone typically has an average zone temperature during desorption that is at least 4° C. higher than the average sorption zone temperature during sorption. For example, desorption can be carried out at an average sorption zone temperature of at least 5° C., or at least 6° C. above that for sorption of the sorbate. Desorption of the sorbate can be carried out at a temperature that is 4° C. to 200° C. greater than that for sorption of the sorbate.

Optionally, a sweep fluid is used for the desorption and/or to assist desorbing the C2 composition. Typical sweep fluids include relatively inert liquids and vapors, especially those which are relatively easy to separate from the desorbed $C_2$ composition. Steam and/or molecular nitrogen are suitable sweep fluids. $C_2$ unsaturates can be separated from the $C_2$ composition, e.g., for storage and/or further processing, such as the polymerization of ethylene obtained from the $C_2$ composition. Desorption is typically continued until the amount of the desired sorbate in the desorption effluent is less than a pre-determined amount, after which the desorption can be halted. Although desorption can be carried out in equilibrium, desorption is typically carried out under kinetic desorption conditions, particularly when the flow-through reactor is a reverse-flow reactor.

In certain aspects, desorption of the sorbate, i.e., desorption of the olefin sorbed from the reaction mixture, is carried out in the flow-through reactor's sorption zone at an average temperature that is less than that of the average temperature in the flow-through reactor's catalytic hydrocarbon conversion zone reaction during the catalytic hydrocarbon conversion, e.g., at least 400° C. less. Average zone temperature of any zone is calculated as the arithmetic mean temperature of the zone. At least two pints are utilized in determining average zone temperature, typically a first point proximate to a first end of the zone and a second point proximate to the opposite end. It is preferable to utilize at least a third point, e.g., one located proximate to the center of the zone.

Reverse-Flow Reactors

Catalytic regenerative, reverse-flow reactors can be used to carry out the hydrocarbon conversion. A regenerative, reverse-flow reactor is (i) "reverse flow" in the sense that an upstream region of the reactor with respect to the average flow of a first feed mixture corresponds to the downstream region with respect to the average flow of a second feed mixture and (ii) "regenerative" in the sense that at least a portion of any heat lost (e.g., by radiation) during the specified catalytic conversion of the specified first feed mixture is provided by the specified catalytic hydrocarbon conversion of the specified second feed mixture. Reverse-flow reactor cycles typically are either symmetric or asymmetric. Asymmetric cycles are typically used to execute endothermic chemistry, and the desired endothermic chemistry is paired with a different chemistry that is exothermic (typically combustion) to provide heat of reaction for the endothermic reaction.

A variety of reverse-flow reactors can be utilized, e.g., alone or in combination with other flow through reactors, including other reverse-flow reactors. For example, a reverse-flow reactor may include a housing, a plurality of input means (e.g., conduits and valves), one or more insulation components (e.g., insulation bricks) and one or more process flow components (e.g., thermal mass, mixing components, etc.). The housing may be utilized to enclose an interior region and has one or more insulation components disposed adjacent to the housing. The plurality of input means may include one or more conduits and one or more valves that are configured to manage the flow of one or more streams into the interior region from a location external to the interior region or housing, e.g., via first and second apertures. Process flow components can be configured and/or arranged to manage the flow of fluids through the interior region, wherein the one or more process flow components may include a thermal mass having different portions with each having different flow-paths and wetted area. In aspects where the first and/or second mixtures are combined in a reverse-flow reactor, one or more mixer or mixer-distributors can be used for the mixing. Regenerative reverse-flow reactors may involve multiple steps repeated in sequence to form a cycle for the process. That is, the specified catalytic hydrocarbon conversion can include two or more sequential steps, which include an optional regeneration step to heat or preheat the zones containing the thermal mass and an oxidative coupling reaction step that converts the hydrocarbons in a first feed mixture into a first reaction mixture during catalytic hydrocarbon conversion mode. When the specified catalytic hydrocarbon conversion is net exothermic or insufficiently exothermic to make-up heat losses resulting from, e.g., one or more of convection, additional regeneration can be provided during an additional regeneration mode. The additional regeneration can be carried out by conducting a heated utility fluid though the reverse-flow reactor. Alternatively or in addition, a flow of at least one combustion mixture of fuel, oxidant, and/or a supplemental amount of one of these reactants, can be provided directly to a location along the flow path within the reactor (e.g., a mixing zone). The delivered reactants in the combustion mixture then exothermically react (combust) and heat the thermal mass. According to one aspect, the combustion reaction can be carried out to heat the thermal masses before, during and/or after one or more intervals of the oxidative coupling reaction. For example, a combustion reaction can be carried out to initially heat (e.g., preheat) one or more thermal masses of the reverse-flow reactor. Combustion products can then be exhausted and a first feed mixture, such as a combination of alkane and oxidant, can be introduced into the reactor and exposed to the heated catalyst in order to catalytically transfer hydrogen in a reacting zone from the first feed mixture's alkane to the first feed mixture's oxidant.

In certain aspects, the flow-through reactor comprises at least one reverse-flow reactor. The reverse-flow reactors can be similar in form to those conventional reverse-flow reactors used for cracking substantially saturated hydrocarbons to produce acetylene, e.g., those described in U.S. Pat. Nos. 7,943,808, 7,491,250, 7,846,401, and 7,815,873. The reverse-flow reactors of the invention differ from conventional reverse-flow reactors in that the reverse-flow reactors of the invention contain at least one of the specified catalytic hydrocarbon conversion catalysts in the specified location with respect to at least one thermal mass.

The reverse flow reactor can be operated similarly to the previously-described flow-through reactors, except that in at least one step of the process (e.g., the thermal mass regeneration step and/or the sorbent desorption step) is carried out in reverse-flow. In other words, the specified feed mixture can be admitted to the first aperture of the revere-flow reactor, with the specified feed mixture then transiting the reverse-flow reactor downstream toward the quench zone. The quenched reaction mixture is conducted away from the second aperture of the reverse-flow reactor, e.g., for removal of the desired $C_{3-}$ olefin. Flow of the feed mixture is then lessened or substantially halted. In aspects where the catalytic hydrocarbon reaction is net-exothermic, a flow of utility fluid flow can then be established in the reverse-flow direction (reverse with respect to the average flow of feed mixture and reaction mixture) in order to remove heat from one or more regions of the reverse-flow reactor. For example, a cool utility fluid (e.g., one at ambient temperature) can be introduced into the second aperture of the reverse-flow reactor, with the utility fluid flowing downstream (with respect to average flow of the utility fluid) toward the flow-through reactor's quench zone. Heat is transferred to the utility fluid in the quench zone, e.g., heat the cooled utility fluid to restore the quench zone to substantially its initial average temperature at the start of forward-flow. The heated utility fluid continues to transit the reverse-flow reactor downstream toward the catalytic hydrocarbon conversion zone. Heat is transferred to the heated utility fluid in the catalytic hydrocarbon conversion zone, e.g., to further heat the heated utility fluid and to restore that zone substantially to an average temperature suitable for carrying out the catalytic hydrocarbon conversion in a subsequent forward flow. Since cooled utility fluid is introduced into the second aperture of the reverse-flow reactor, with the further-heated utility fluid removed from the first aperture, heat transfer to the utility fluid will (i) restore the hydrocarbon conversion catalyst of the catalytic hydrocarbon conversion zone to an average temperature in the range of 550° C. to 1100° C. and (ii) restore that portion of the thermal mass (the first portion) located in the quench zone to an average temperature such that [the hydrocarbon conversion catalyst's average temperature—the first portion of the thermal mass's average temperature] is ≥50° C. Operating this way, reverse-flow reactors can overcome certain difficulties encountered in the operation of unidirectional-flow flow-through reactors for the specified catalytic hydrocarbon conversion, e.g., the need for additional cooling of the quench zone during the regeneration step of unidirectional-flow reactors in continuous operation, e.g., additional heat transfer away from the first portion of the thermal mass.

Certain aspects of the invention will now be described with respect to a reverse-flow reactor having first and second heat-transfer zones and a catalytic hydrocarbon conversion zone, at least a portion of the catalytic hydrocarbon conversion being located between the first and second heat-transfer zones. The invention is not limited to these aspects, and this description is not meant to foreclose other embodiments within the broader scope of the invention.

Referring now to FIG. 1A, a reverse flow reactor is provided, the reverse-flow reactor having first and second regions. The first region comprises a first heat transfer zone and a first portion of a catalytic hydrocarbon conversion zone. The second region comprises a second heat-transfer zone, and a second portion of the catalytic hydrocarbon conversion zone. The first heat transfer zone contains a first thermal mass $M_1$. The second heat transfer zone contains a second thermal mass $M_2$. $M_1$ and $M_2$ can be selected from among the specified thermal masses, e.g., from thermal masses having the same composition and form as those specified in connection with the uni-flow flow-through reactor. $M_1$ and $M_2$ can be of substantially the same size, shape, density, and/or composition, but this is not required. The first and second thermal masses are optionally parts (or portions) of a single monolith, e.g., segments thereof.

The catalyst zone contains one or more of the specified catalytic hydrocarbon conversion catalysts, C. As shown in the figure, portions of the hydrocarbon conversion catalyst are located in both the first and second catalytic hydrocarbon conversion zones, as indicated by the shading. For example, a first portion of the hydrocarbon conversion catalyst can be located in the first portion of the catalytic hydrocarbon conversion zone and a second portion of the hydrocarbon conversion catalyst can be located in the second portion of the catalytic hydrocarbon conversion zone.

First and second feed mixtures are provided, as are first and second utility fluids. The first and second feed mixtures are selected from among the specified feed mixtures. Optionally, the first and second feed mixtures have the same composition. Optionally, the first and second feed mixtures (or components thereof) are obtained from the same source. For example, the first feed mixture's first reactant can be of the same composition as the second feed mixture's first reactant, and both can be obtained from the same source, e.g., natural gas. The first feed mixture's oxidant can have the same composition as the second feed mixture's oxidant, and both can be obtained from the same source, e.g., air. First and second utility fluids are also provided. The first and second utility fluids can be selected from among any of the specified utility fluids. The first and second utility fluids can have the same composition, and can be obtained from the same source, e.g., a steam generator.

At the start of the process, the first thermal mass $M_1$ is heated, e.g., by exposing $M_1$ to a temperature in the range of from 550° C. to 1100° C. The hydrocarbon conversion catalyst C and the second thermal mass $M_2$ can be at ambient temperature. At the start of a first time interval, a flow of the first feed mixture is established into the reverse-flow reactor via its first aperture (not shown). The first feed mixture flows into passages of $M_1$ via end 1 of $M_1$. Heat is transferred from $M_1$ to the first feed mixture in the first heat transfer zone (a pre-heat zone during the first interval) and the heated feed mixture transfers heat to at least the first portion of hydrocarbon conversion catalyst C (and optionally to its second portion). At the start of the first interval, (i) the initial average temperatures of $M_1$ and $M_2$, (ii) the initial average temperature of hydrocarbon conversion catalyst C, and (iii) the flow rate, temperature, and pressure of the first feed mixture are pre-determined to achieve:

A. an initial average temperature in at least the first portion of the hydrocarbon conversion catalyst C in the range of from 550° C. to 1100° C. in the presence of the first feed mixture, and B. an initial average temperature of $M_2$ in the presence of a first reactant mixture produced by the hydrocarbon conversion reaction such that [the initial average temperature of the first portion of the hydrocarbon conversion catalyst C—the initial average temperature of $M_2$] is ≥50° C.

The hydrocarbon conversion reaction can be net endothermic or net exothermic, but is typically net exothermic. The first reaction mixture is the same as that specified as resulting from operating a uni-flow flow-through reactor operating under substantially the same conditions using the specified first feed mixture.

The first reaction mixture flows through passages of $M_2$ and is quenched in the second heat transfer zone (a quench zone during the first time interval) by a transfer of heat from the first reaction mixture to $M_2$. A first quenched reaction mixture is conducted away from end 2 of $M_2$, and out of the reverse-flow reactor via its second aperture (not shown). Olefin, e.g., $C_{3-}$ olefin can be separated from the quenched first reaction mixture downstream of the reverse-flow reactor. Olefin separation can be carried out using one or more of the same methods described in connection with removing olefin from the specified reaction mixtures in uni-flow flow-through reactors.

FIG. 1A also schematically illustrates a temperature profile TP for the reverse-flow reactor during a net exothermic hydrocarbon conversion reaction carried out during the first time interval. Arrows on the TP curve indicate a shift in the position of the peak in TP from upstream to downstream as the first time interval progresses. As the peak in TP progresses downstream, a time will be reached at which the average temperature of $M_2$ is <50° C. cooler than the average temperature of the second portion (the downstream portion) of the hydrocarbon conversion catalyst. This is an indication that the first reaction mixture is not sufficiently quenched. The flow of first feed mixture is then lessened or halted.

Figure 1B:
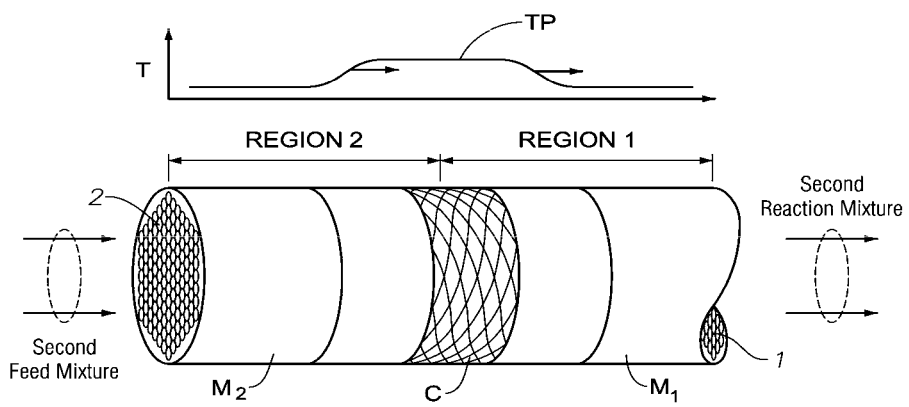

During a second time interval, illustrated in FIG. 1B, reverse flow is initiated by passing the second feed mixture into the reverse-flow reactor through the second aperture (not shown) and into end 2 of $M_2$. Since $M_2$ is heated in the first interval, heat is transferred from $M_2$ to the second feed mixture as the second feed mixture traverses the internal passages of $M_2$. The heated second feed mixture conducted to the upstream portion (the second portion) of hydrocarbon conversion catalyst C, where it is reacted to produce a second reaction mixture. The second reaction mixture can have the same composition as the first reaction mixture.

The second reaction mixture is conveyed through the passages of $M_1$. Heat is transferred from the second reaction mixture to $M_1$, to produce a quenched second reaction mixture. The quenched second reaction mixture is conducted out of end 1 of $M_1$, and then away from the reverse-flow reactor via the first aperture (not shown). The quenched second reaction mixture can be processed in the same way as is the first reaction mixture, e.g., for removal of $C_{3-}$ olefin. The same equipment can processes can be used as is utilized for removing $C_{3-}$ olefin from the quenched first reaction mixture.

The temperature profile TP during the second time interval is also shown in FIG. 1B. As indicated by arrows, the peak in TP shifts away from $M_2$ toward $M_1$ during the second time interval. As the peak in TP progresses downstream, a time will be reached at which the average temperature of $M_1$ is <50° C. cooler than the average temperature of the first portion (the downstream portion) of the hydrocarbon conversion catalyst. This is an indication that the second reaction mixture is not sufficiently quenched. The flow of second feed mixture is then lessened or halted.

The first and second time intervals can be substantially non-overlapping intervals. Each of the first and second time intervals can be, independently, an interval having a duration in the range of from about 0.5 seconds to about 15 seconds. The interval between the first and second time intervals (the "dead-time", which represents the interval of time it takes to reverse flow of the feed mixtures) is preferably as short as possible so that the reverse flow cycle can be as rapid as possible. From a practical standpoint, the dead-time should be, e.g., ≤ than 0.5 seconds, such as in a range of from about 0.01 seconds to about 0.5 seconds. Upon completion of the second time interval, the intervals can be repeated. That is, the flow shown in FIG. 1A can be reinitiated and followed by subsequent reinitiation of the flow shown in FIG. 1B. When operated in a reverse-flow reactor, the process's cycle time is generally ≥0.5 second, such as in the range of 10 seconds to 240 seconds, in the range of 10 seconds to 120 seconds, in the range of 20 seconds to 60 seconds, or in the range of 20 seconds to 40 seconds. The term "cycle time" means the time from a first time interval to the next first time interval, including (i) any intervening time intervals (e.g., second, third, and/or fourth intervals) and (ii) any dead-time between any pair of intervals.

In certain aspects, at least a portion of the hydrocarbon conversion catalyst is located in a region of the reverse-flow reactor that is between the first and second thermal masses. For example, ≥50.0 wt. % of the hydrocarbon conversion catalyst, based on total weight of the hydrocarbon conversion catalyst, can be located in a zone between the first and second regions. The first and second regions can be separate, non-overlapping regions of the reverse-flow reactor. In other aspects, at least part of the hydrocarbon conversion catalyst is located on or in the passages of $M_1$ and/or $M_2$. For example, (i) ≥50% (weight basis) of the first portion of the hydrocarbon conversion catalyst can be located in the passages of $M_1$ and (ii) ≥50% (weight basis) of the second portion of the hydrocarbon conversion catalyst can be located in the passages of $M_2$.

A portion of $M_1$ can be located outside the first heat transfer zone and/or a portion of $M_2$ can be located outside the second heat transfer zone. In certain aspects, (i) ≥50.0% of $M_1$ is located in the first heat-transfer zone, with any remaining portion located in that part of catalytic hydrocarbon conversion zone that is proximate to $M_1$, and (ii) ≥50.0% of $M_2$ is located in the second heat-transfer zone, with any remaining portion located in that part of catalytic hydrocarbon conversion zone that is proximate to $M_2$.

Optionally, the reverse-flow reactor comprises first and second sorbents. The first and second sorbents can be one or more of those sorbents specified in connection with a uni-flow flow-through reactor. The first and second sorbents typically have the same composition. Certain aspects utilizing first and second thermal masses and first and second sorbents are illustrated schematically in FIGS. 2A and 2B. The invention is not limited to these aspects, and this description is not meant to foreclose other aspects within the broader scope of the invention.

Figure 2A:
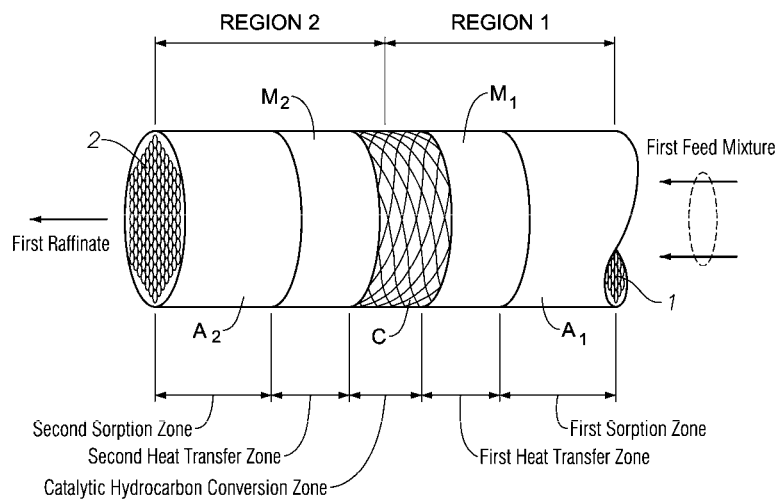
FIGS. 2A and 2B are simplified diagrammatic illustrations of certain process steps in a regenerative reverse-flow reactor system including reaction and olefin sorption zones.
Figure 2B:
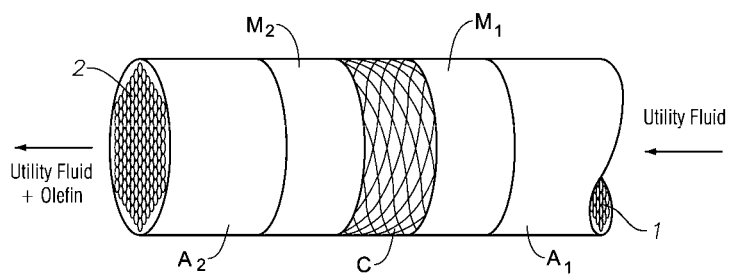

As shown in FIGS. 2A and 2B, the first and second thermal masses $M_1$ and $M_2$ are monolithic honeycombs (e.g., of refractory such as ceramic) having internal passages for the flow of first and second feed mixtures and first and second reactants as the case may be. $M_1$ and $M_2$ can be selected from among the specified thermal masses, e.g., from thermal masses having the same composition and form as those specified in connection with a uni-flow flow-through reactor. First sorbent $A_1$ is located proximate to $M_1$, and is in the form of a honeycomb monolith comprising internal passages, the internal passages containing at least a portion of the first sorbent, which is exposed to the flow of the first feed mixture, the second reactant mixture, a second raffinate, and at least a second utility fluid. Second sorbent $A_2$ is located proximate to $M_2$, and is in the form of a ceramic honeycomb monolith comprising internal passages, the internal passages containing at least a portion of the second sorbent, which is exposed to the flow of the second feed mixture, the first reactant mixture, a first raffinate, and at least a first utility fluid. $A_1$ and $A_2$ can be selected from among the specified sorbents, e.g., from sorbents having the same composition and form as those specified in connection with a uni-flow flow-through reactor. The first and second sorbents are typically selective for sorbing $C_2$ hydrocarbon, e.g., for sorbing ethylene, under kinetic sorption conditions.

In the aspects illustrated in FIGS. 2A and 2B, the reverse-flow reactor further comprises at least one hydrocarbon conversion catalyst. The hydrocarbon conversion catalyst is located within passages of a honeycomb monolith C, e.g., in the form of one or more of the specified catalysts as particles and/or layer(s) on the internal surfaces of passages within monolith C. Catalyst monolith C is located between thermal mass monoliths $M_1$ and $M_2$. Thermal mass monolith $M_1$ is located between sorbent monolith $A_1$ and catalyst monolith C. Thermal mass monolith $M_2$ is located between sorbent monolith $A_2$ and catalyst monolith C. $A_1$, $M_1$, and 50% of C are located in a first region of the reverse-flow reactor. $A_2$, $M_2$, and the remaining 50% of C are located in a second region of the reverse-flow reactor. The reverse-flow reactor's catalytic hydrocarbon conversion zone includes C. The reverse-flow reactor's first sorption zone includes $A_1$, and the second sorption zone includes $A_2$. The reverse-flow reactor's first heat transfer zone includes $M_1$, and the second heat transfer zone includes $M_2$. Except for heat transfer to/from the catalytic hydrocarbon conversion zone and to/from the first and second sorption zones, the zones are substantially non-overlapping.

At the start of the process, first sorbent $A_1$ and first thermal mass $M_1$ are heated, e.g., by exposing them to a temperature in the range of from 550° C. to 1100° C. The hydrocarbon conversion catalyst C, the second thermal mass $M_2$, and second sorbent $A_2$ can be at ambient temperature. At the start of a first time interval, a flow of the first feed mixture is established into the reverse-flow reactor via its first aperture (not shown). The first feed mixture flows into passages of $A_1$ via end 1, and transits the internal passages of $A_1$ and $M_1$. Heat is transferred from to the first feed mixture to $M_1$ and optionally $A_1$ in the first heat transfer zone (a pre-heat zone during the first interval). The heated first feed mixture transfers heat to the hydrocarbon conversion catalyst C in the catalytic hydrocarbon conversion zone. At the start of the first interval (ii) the initial average temperature of hydrocarbon conversion catalyst C, (ii) the flow rate, temperature, and pressure of the first feed mixture, and (iii) the initial average temperatures of $M_1$, $M_2$, $A_1$, and $A_2$ are pre-determined to achieve:

A. an initial average temperature of hydrocarbon conversion catalyst C in the range of from 550° C. to 1100° C. in the presence of the first feed mixture,
B. an initial average temperature of $M_2$ in the presence of a first reactant mixture produced by the hydrocarbon conversion reaction such that [the initial average temperature of the first portion of the hydrocarbon conversion catalyst C—the initial average temperature of $M_2$] is ≥50° C., and
C. an initial average temperature of $A_2$ such that [the initial average temperature of $M_2$ the initial average temperature of $A_2$] is ≥50° C.

The hydrocarbon conversion reaction can be net endothermic or net exothermic, but is typically net exothermic. The first reaction mixture is the same as that specified as resulting from operating a uni-flow flow-through reactor operating under substantially the same conditions using the specified first feed mixture.

The first reaction mixture flows through passages of $M_2$ and is quenched in the second heat transfer zone (a quench zone during the first time interval) by a transfer of heat from the first reaction mixture to $M_2$. A first quenched reaction mixture is conducted away from $M_2$, and then through the internal passages of $A_2$. At least a portion of the $C_2$ hydrocarbon is sorbed from the quenched first reaction mixture in $A_2$. A first raffinate (depleted in $C_2$ hydrocarbon) is conducted away from $A_2$ via end 1. The first raffinate can be conducted away from the reverse-flow reactor via its second aperture (not shown), e.g., for removing from the raffinate at least a portion of any remaining additional $C_2$ hydrocarbon. During the first time interval, the peak in the reverse-flow reactor's temperature profile TP (not shown) shifts away from $A_1$ and $M_1$ toward $M_2$ and $A_2$.

Within a predetermined time before, at, or after breakthrough of the desired sorbate from $A_2$, the passing of the first reaction mixture to the reverse-flow reactor can be lessened or discontinued, in order to desorb sorbate from $A_2$. This can be carried out during a second time interval as shown in FIG. 2B.

During the second time interval, a first utility fluid is conducted into the reverse-flow reactor's first aperture (not shown). The utility fluid transits the internal passages of $A_1$ and $M_1$, optionally absorbing heat from those monoliths to further cool them. The utility fluid then transits the internal passages of monolith C, and absorbs heat in the reverse-flow reactor's catalytic hydrocarbon conversion zone to cool the hydrocarbon conversion catalyst. Additional heat is transferred to the utility fluid as it transits the internal passages of $M_2$, which cools $M_2$. Heat is transferred from the heated utility fluid to $A_2$ in order to desorb the sorbate. In other words, the flow of first utility fluid further displaces the peak of temperature profile TP away from $M_2$ toward $A_2$. The flow of first utility fluid is typically maintained until the amount of the desired sorbate in the first utility fluid is less than a pre-determined amount, after which the desorption can be halted. Desorption conditions can be the same as those specified for use in connection with uni-flow flow-through reactors. Typically, desorption is carried out under kinetic desorption conditions. $C_2$ hydrocarbon can be removed from the rich first utility fluid by conventional methods, but the invention is not limited thereto.

Following desorption, the flow of first utility fluid is lessened or substantially halted. A second feed mixture is then introduced into the reverse-flow reactor in an average flow direction that is opposite to the average flow direction during the first and second time intervals. When the reverse-flow reactor is physically symmetric about an imaginary line separating the first and second regions, as shown in FIGS. 2A and 2B, and the second feed mixture is substantially the same as the first feed mixture, the second reaction mixture is processed to produce a second raffinate having substantially the same composition as the first raffinate. In other words, the reactor can be operated the same way as during the first time interval, but in the reverse direction. A second utility fluid can be utilized for desorbing the desired sorbate from $A_1$, and for restoring A2, $M_2$, C, $M_1$, and $A_1$ to conditions suitable for re-introducing the first feed mixture into the reverse-flow reactor's first aperture.

The time intervals during which (i) catalytic conversion of reactant and oxidant is carried out in the forward direction, (ii) desorption is carried out in the forward direction, (iii) catalytic reaction of reactant and oxidant is carried out in the reverse direction, and (iv) desorption is carried out in the reverse direction, e.g., the first, third, second, and fourth time intervals, can be non-overlapping time intervals. The process can be carried out repetitively, if desired, e.g., by repeating a cycle of first time interval, third time interval second time interval, and fourth time interval. Dead-time between adjacent time intervals is generally ≤0.5 seconds, e.g., ≤0.25 seconds. In the aspects illustrated in FIGS. 2A and 2B, the process's cycle time is generally ≥0.5 second, such as in the range of 10 seconds to 240 seconds, in the range of 10 seconds to 120 seconds, in the range of 20 seconds to 60 seconds, or in the range of 20 seconds to 40 seconds. Relatively longer cycle times are typically encountered over those of aspects illustrated in FIGS. 1A and 1B, as a result of the desirability of desorbing $C_2$ sorbate from sorbent located in the reverse-flow reactor (e.g., $A_1$ and $A_2$).

In the present disclosure, a reactor refers to equipment used for chemical conversion. As such, several items identified as reactors may be combined to become a single entity that is also identified as a reactor, in that individual and combined entities may be characterized as equipment used for chemical conversion. Accordingly, a plurality of reverse flow reactors can be utilized together, e.g., in series, parallel, and/or series-parallel. For example, a system of two reverse-flow reactors can be operated in series. In a first step, a first feed mixture is passed to a first stage of a reactor that includes a heated first thermal mass and a second thermal mass. The first feed mixture can be heated with the heated first thermal mass, and the heated first feed mixture can be contacted in the first stage with a first hydrocarbon conversion catalyst to convert at least a portion of the alkane to alkene, producing an alkene-containing first stage reaction mixture. The first reaction mixture is then quenched by transferring heat from the first reaction mixture to the second thermal mass. At least a portion of the alkene can be separated from the quenched first stage reaction mixture to produce first stage raffinate comprising water, any remaining alkene, and unconverted alkane from the first stage reaction mixture. The first stage raffinate can be transferred to a second stage of the reactor, with the second stage including third and fourth thermal masses, the third thermal mass being a heated thermal mass at the start of transfer of the first stage raffinate to the second stage of the reactor. The first stage raffinate can be heated with the heated third thermal mass; and the heated first stage raffinate can be contacted in the second stage with a second hydrocarbon conversion catalyst to convert at least a portion of the unconverted alkane in the first stage raffinate to alkene, producing an alkene-containing second stage reaction mixture. The second stage reaction mixture is then quenched by the fourth thermal mass by transferring heat from the second stage reaction mixture to the fourth thermal mass. At least a portion of the alkene can be removed from the quenched second stage reaction mixture to produce a second stage raffinate. Flowing the first feed mixture to the reactor can then be lessened or discontinued. A second feed mixture, which can be of the same composition as the first feed mixture, is then passed to the series reactor system in an average flow direction that is opposite to the first feed mixture's average flow direction.

EXAMPLE

Figure 3:
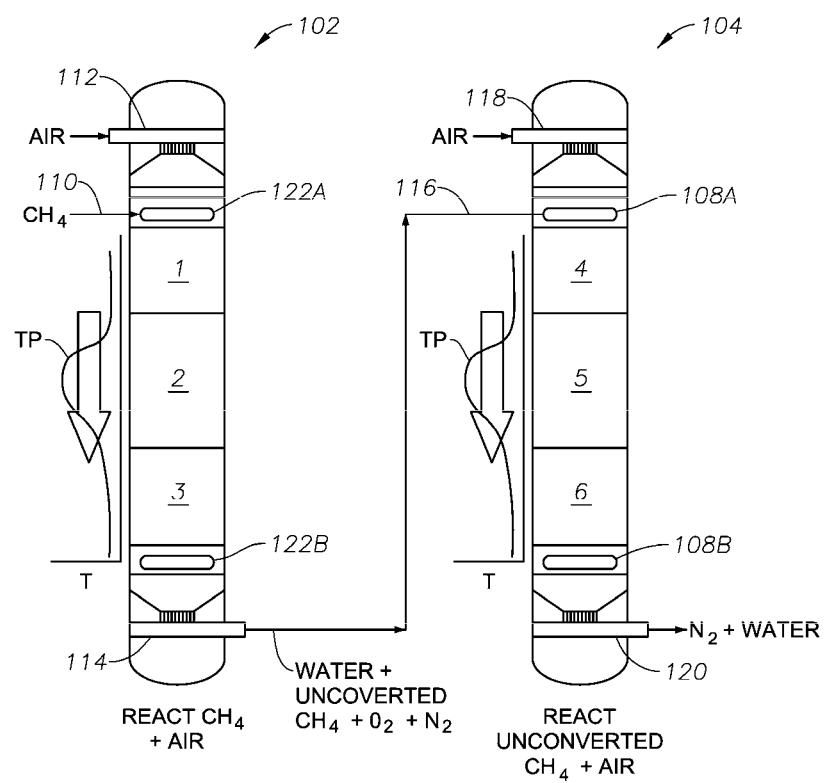
FIG. 3 is a simplified diagrammatic illustration of a two stage reverse-flow reactor utilized for converting a feed into conversion products containing olefins in accordance with certain aspects the invention.
Figure 4:
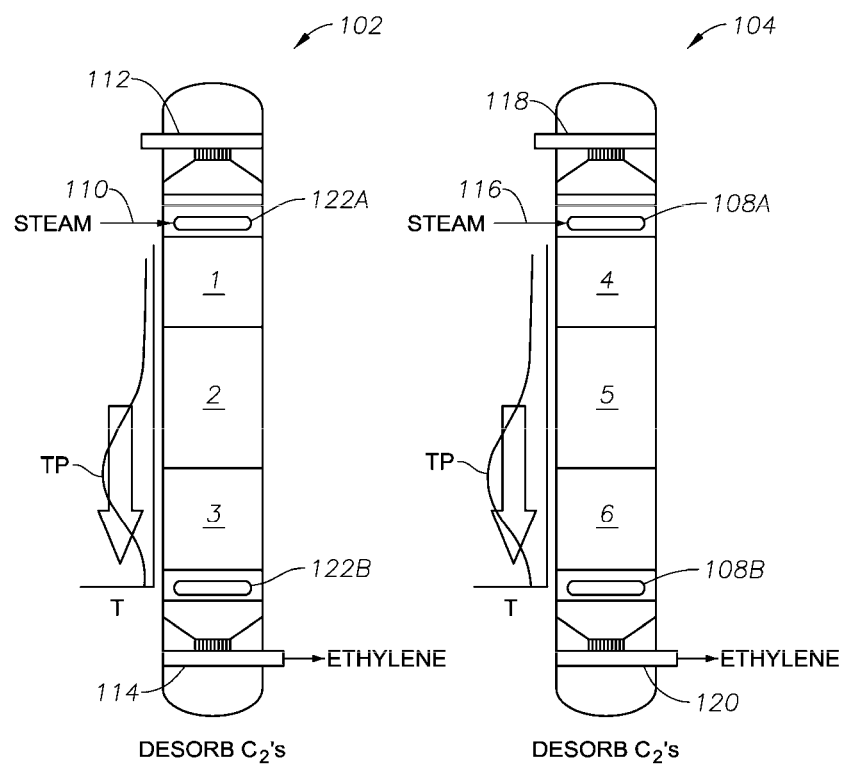
FIG. 4 is a simplified diagrammatic illustration of desorbing olefin from the two stage reverse-flow reactor in accordance with certain aspects the invention.
Figure 5:
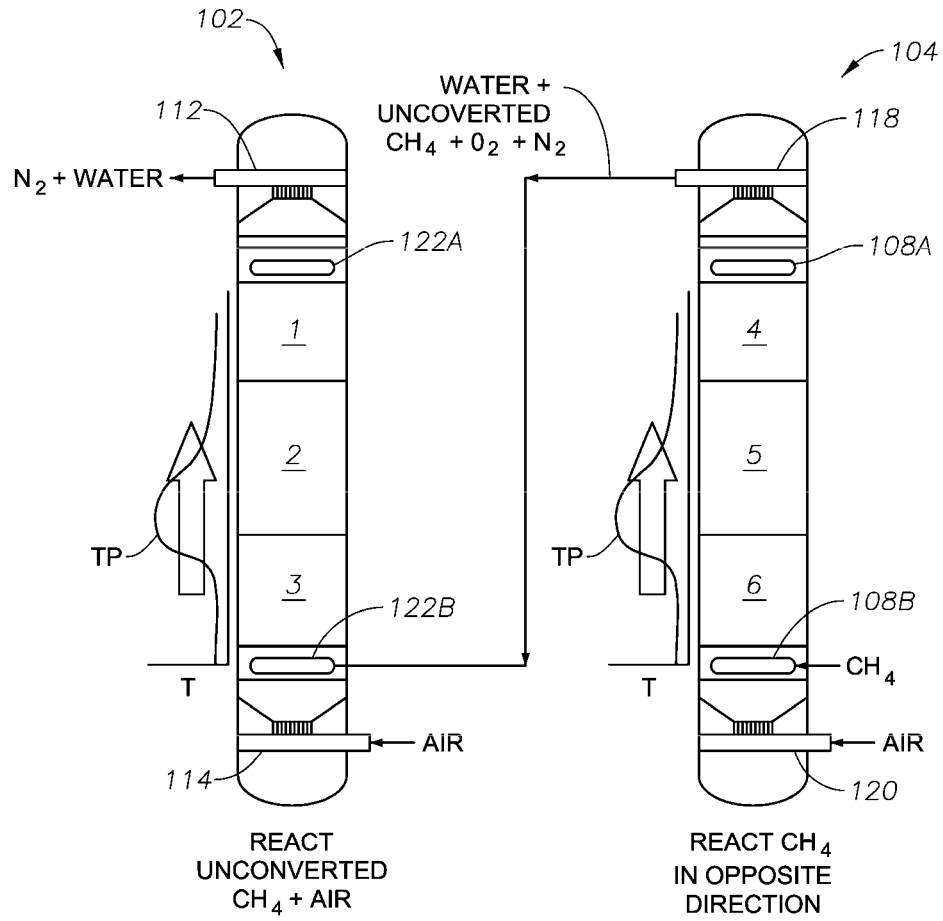
FIG. 5 is a simplified diagrammatic illustration of a reverse flow of feed through the two stage reverse-flow reactor in accordance with certain aspects the invention.

An example of a reverse-flow reactor system utilized for the specified catalytic hydrocarbon conversion is depicted in FIGS. 3-5. The reactor comprises two reactor stages 102 and 104. The first reactor stage 102 comprises Zones 1-3. Zone 1 in includes first heat transfer and first sorption functionalities. Zone 2 includes catalytic hydrocarbon conversion functionality. Zone 3 includes second heat transfer and second sorption functionalities. The second reactor also includes three zones. Zone 4 in includes first heat transfer and first sorption functionalities. Zone 5 includes catalytic hydrocarbon conversion functionality. Zone 6 includes second heat transfer and second sorption functionalities. Zones 1 and 4 each include (i) a first thermal mass selected from among the specified thermal masses and (ii) a first sorbent selected from among the specified sorbents. Zones 2 and 5 each include at least one of the specified hydrocarbon conversion catalysts. Zones 3 and 6 each include (i) a second thermal mass selected from among the specified thermal masses and (ii) a second sorbent selected from among the specified sorbents.

It is understood that one or more valves and other flow control devices (e.g., check valves, louvers, flow restrictors, timing systems, etc.) can be used to control fluid flow through reactor stages 102 and 104, which include first and second feed mixtures, and an optional utility fluid (e.g., a gas such as sweep gas). For example, a means for conveying fuel, oxidant, reactant, alkane feed mixture, and/or utility fluid (e.g., via conduits 110, 112, 114, 116, 118, and 120) into the appropriate passages in the first and second reactor stages may include one or more of plenums, valves, vanes, spargers, and/or distributors. Suitable spargers, distributors, etc., are disclosed in U.S. Pat. No. 7,815,873, which is incorporated by reference herein in its entirety. Although the invention is compatible with conventional spargers, distributors, plenums, etc., it is not limited thereto, and this description is not meant to foreclose other flow-control means within the broader scope of the invention.

The specified hydrocarbon conversion reaction progresses from the first stage 102 to the second stage 104. At the start of a first time interval, illustrated in FIG. 3, Zones 1-3 and Zones 4-6 are at substantially the same conditions specified for the first step of the aspects illustrated in FIGS. 2A and 2B. During the first time interval, a first reactant selected from among one of the feed mixture's specified reactants is conducted through conduit 110 to first distributor 122A, which directs the flow of the first reactant into the first reactor stage 102. A first oxidant (e.g., oxygen, such as oxygen obtained from air or oxygen in air air) is conducted separately via conduit 112 into the first reactor stage 102. The first reactant and oxidant flow through passages of the first thermal mass and first sorbent, in comparable flow as previously described with regard to FIG. 2A. The first reactant and the first oxidant can be combined to produce the first feed mixture upstream of Zone 1. In other aspects, the first reactant and first oxidant are conveyed through separate channels of the first thermal mass, with the heated first reactant and heated first oxidant then being combined to produce a heated first feed mixture upstream of Zone 2. In still other aspects, one component of the first feed mixture, e.g., one of diluent, first reactant, or first oxidant, is conducted through the at least one channel of the first thermal mass (for heating that component and cooling the first thermal mass. The other first feed mixture component(s) are conducted, e.g., via a conduit external to the reverse-flow reactor, to a location upstream of Zone 2, where these components are introduced into the first stage reactor 102. The first feed mixture's reactant and oxidant can be combined downstream of Zone 1 but upstream of Zone 2 to produce the heated first feed mixture. So long as (i) sufficient heat is provided to the first feed mixture from the first thermal mass to accomplish the specified catalytic reaction in zone 2, it is not necessary for both the first reactant and the first oxidant to pass through the passages of the first thermal mass. The heated first feed mixture is then conducted to Zone 2.

In aspects illustrated in FIG. 3, the passages of the reactor Zone 2 contain at least one of the specified hydrocarbon conversion catalysts, for converting at least a portion of the heated first feed mixture's alkane to $C_{2+}$ olefin. The $C_{2+}$ olefin is a component of a first-stage reaction mixture produced in Zone 2, the first-stage reaction mixture further comprising at least a portion of any by-products of the reaction (e.g., water), at least a portion of any unconverted first feed mixture or components thereof, and at least a portion of any unreacted diluent (e.g., unreacted nitrogen when the oxidant is molecular oxygen in air). Heat is transferred from the first-stage reaction mixture to the second thermal mass in Zone 3 to produce a quenched first stage reaction mixture.

A temperature profile TP is shown along first reactor stage 102 in FIG. 3. When a net exothermic catalytic hydrocarbon conversion reaction is carried out in Zone 2, the peak of temperature profile TP exhibits an increasing temperature. TP then exhibits a decreasing temperature as heat is transferred from the flowing first-stage reaction mixture to the second thermal mass during quenching. As shown by the arrow, the peak in TP moves away from Zone 1 toward Zone 3 during the first time interval. At least a portion of the quenched first-stage reaction mixture's olefin is sorbed by the first sorbent as the quenched second-stage reaction mixture transits Zone 3.

A quenched first-stage reaction mixture depleted in olefin (a first-stage raffinate) is passed to second stage 104 via conduit 116 to a sparger 108A. The first-stage raffinate comprises unconverted alkane, and at least a portion of any (i) unconverted oxidant and/or (ii) unreacted any unreacted diluent (e.g., unreacted nitrogen, when the oxidant is molecular oxygen in air). If needed to maintain the alkane:oxidant molar ratio in the specified range, additional oxidant (e.g., oxygen in air or obtained from air) can be conducted via conduit 118 into the second reactor stage 104 for combining with the first-stage raffinate in second reactor 104.

The first-stage raffinate and additional oxidant flow through a first heated thermal mass, analogous to the first thermal mass of Region 1 in FIG. 2A. Heat is transferred from the heated first thermal mass to the first-stage raffinate as the raffinate transits Zone 4. At least a portion of the additional oxidant is added to the heated first-stage raffinate upstream of Zone 5. Zone 5 contains passages which include at least one of the specified hydrocarbon conversion catalysts, for converting unconverted alkane in the first-stage raffinate to a second-stage reaction mixture comprising $C_{2+}$ olefin produced in Zone 5, at least a portion of (i) any reaction by-products (e.g., water), (ii) any unconverted additional oxidant, and (iii) any unconverted first-stage raffinate or components thereof (including any $C_{2+}$ olefin from the first-stage raffinate). When the hydrocarbon conversion reaction of Zone 5 is net exothermic, the peak in TP moves in the direction of Zone 6, as shown in the temperature profile along reactor stage 104.

As the second-stage reaction mixture pass away from reaction Zone 5, its components are further mixed and passed through the second thermal mass of second reactor 104, located in Zone 6. Heat is transferred to the second thermal mass from the second-stage reaction mixture in Zone 6 to produce a quenched second-stage reaction mixture. At least a portion of the quenched second-stage reaction mixture's olefin is sorbed by the second sorbent of second reactor 104, located in Zone 6. A second-stage raffinate (the quenched, olefin-depleted, second-stage reaction mixture) exits the second reactor stage 104 through the conduit 120. The second-stage raffinate typically comprises unreacted by-products of the catalytic hydrocarbon conversion of Zones 2 and/or 5, e.g., water. The second-stage raffinate typically further comprises at least a portion of (i) any unconverted first mixture or components thereof, (ii) any unconverted diluent (e.g., unconverted nitrogen when the oxidant and/or additional oxidant is molecular oxygen in air, and (iii) any unconverted additional oxidant.

After a first time interval, the flow of first reactant and first oxidant to reactor stage 102 are stopped (as in any additional oxidant, provided to reactor 104). During a second time interval, the sorbed olefins (sorbate) of Zones 3 and 6 are desorbed. During the third time interval, a heated utility fluid, which can be selected from among any of the specified utility fluids, e.g., steam, is flowed through the reactor 102 and/or reactor 104. Heat is transferred from the heated utility fluid to the sorbents of Zone 3 and/or Zone 4, to release (e.g., desorb) olefin. The cooled utility fluid is utilized as a sweep gas, e.g., as a moving force to remove the olefin remaining in the reactor. Besides steam, utility fluid can be selected from among one or more of nitrogen, substantially inert gas such as argon, etc. When the utility fluid is steam, conventional methods can be utilized to (i) condense the steam and (ii) to separate desorbed olefin from the condensed steam.

As shown in FIG. 4, steam is utilized as the heated utility fluid. The steam is conducted through conduits 110 and 116 of first and second reactor stages 102, 104, respectively. As the utility fluid passes through the reactor stages, the high temperature region of the temperature profiles for reactors 102 and 104 decrease in peak temperature and shifts downstream (with respect to utility fluid flow) as indicated by profiles TP alongside each reactor stage. For example, as the steam is flowed through the reactor stages, the portion of thermal masses located in Zones 3 and 6 are eventually heated to a temperature in the range of from 200° C. to 600° C., e.g., about 400° C. At a temperature in this range, the sorbent of Zones 3 and 6 is less selective to the desired sorbate, e.g., $C_2$ hydrocarbon, such as ethylene. This means that as the temperature in the sorbent zones increases, sorbate can be readily desorbed and removed via conduits 114 and 120. Following desorption, the flow of steam is lessened or substantially halted. If needed, a combustion interval can be utilized for restoring the temperatures of thermal masses located in regions 1-6 before the flow of reactants is provided in the reverse direction (for the second time interval). Typically, utility fluid flow (and sorbate desorption) is substantially halted before ≥10% of the area under curve TP is downstream of Zones 3 or 6. In those aspects, little or no combustion is needed for reactor pre-heating. This represents a balance between advantageously desorbing more olefin and disadvantageously losing heat from the reactor. Kinetic sorption and desorption conditions are typically used, and the durations of the process's cycle times are typically selected accordingly.

Since the reverse-flow reactors of FIGS. 3 and 4 are substantially symmetric, the reaction can be carried out in reverse-flow mode under substantially the same conditions. FIG. 5 depicts an example of reverse flow relative to the flow shown in FIG. 3. Reverse flow is carried out in a third time interval following the second time interval. As shown in FIG. 5, a second reactant, which can be selected from among any of the reactants specified for use as a first reactant, is conducted through sparger 108B of reactor 104. A second oxidant, which can be selected from among any of the oxidants specified for use as a first oxidant, is conducted into reactor 104 through conduit 120. The second reactant can be of the same composition as the first reactant, and the second oxidant can be of the same composition as the first oxidant, but this is not required.

The second reactant and second oxidant flow through separate passages or channels of the heated second thermal mass (heated by the utility fluid during the desorption) located in Zone 6. For example, the second reactant can flow through the second thermal mass via a reactant passage or reactant channel(s), and the second oxidant can flow through the second thermal mass via an oxidant passage or oxidant channel(s). The reactant and oxidant streams are heated and mixed together prior entering reactor Zone 5, forming a second feed mixture analogous to the second feed mixture of the aspects illustrated in FIG. 1B. Except for flow direction, the flow conditions, reactor temperature profiles, reactant, oxidant, reaction products, etc., in reverse-flow (second time interval as shown in FIG. 5) can be substantially the same as those of the first time interval (as shown in FIG. 3).

When an exothermic the hydrocarbon conversion reaction is carried out in Zone 5, the peak of TP for reverse-flow reactors 102 and 104 moves in the direction of Zones 1 and 4. The temperature decreases in in Zones 6, resulting from the transfer of heat from the second thermal mass to the second reactant and/or second oxidant. The temperature of the TP increases in Zone 4, as a result of heat transfer to the first thermal mass from the first-stage reaction mixture. As is clear from the figure, when operating in reverse-flow the first stage is reactor 104 and the second stage is reactor 102. This heat transfer produces a quenched first-stage reaction product. At least a portion of the first-stage reaction mixture's olefin is removed in Zone 4 by the first sorbent.

A first-stage raffinate is passed to second stage 102 via sparger 122B. The first raffinate (and second stage reaction mixture) flow through Zones 1-3, is in reverse flow with regard to FIG. 3. Additional oxidant can be added, if needed to maintain the specified alkane:oxidant molar ratio, via sparger 114. The additional oxidant can be substantially the same as that utilized in the aspects shown in FIG. 3, in substantially the same amount.

Heat is transferred to the first-stage raffinate from the second thermal mass of reactor 102. The heated first-stage raffinate is passed through distribution means (e.g., one or more mixer/distributors) prior entering Zone 2, for converting at least a portion of the heated first-stage raffinate's alkane and at least a portion of (i) any oxidant in the first-stage raffinate and (ii) any additional oxidant in the presence of the hydrocarbon conversion catalyst located in reactor 102 to produce a second-stage reaction mixture comprising $C_{2+}$ olefin. Heat is transferred from the second-stage reaction mixture to the first thermal mass located in Zone 1 to produce a quenched second-stage reaction mixture. As seen in a temperature profile TP along reactor stage 102, when an exothermic hydrocarbon conversion reaction is carried out in the Zone 2, the peak of TP moves toward zone 1.

At least a portion of the second-stage reaction mixture's $C_{2+}$ olefin is selectively removed by the first sorbent of reactor 102, located in Zone 1. A second-stage raffinate is conducted away from Zone 1 via conduit 112. A desorption time interval (e.g., a fourth time interval) can be utilized for desorbing at least a portion of the olefin sorbed in Zones 1 and 4. The desorbtion can be substantially the same as that illustrated in FIG. 4, but with the flow of steam in the reverse direction. When (i) reactors 102 and 104 are substantially identical and contain substantially identical components, (ii) when the first feed mixture has substantially the same composition as the second feed mixture, and (iii) when substantially the same process conditions (temperature, pressure, flow rate) subsist in the first and second stages in forward-flow-mode and in reverse-flow mode, then (iv) the composition of the second-stage raffinate in forward-flow mode will be substantially the same as that is reverse-flow mode and the desorbed $C_{2+}$ olefin stream desorbed in forward-flow mode is substantially the same as that desorbed in reverse-flow mode.

By utilizing a system comprising a plurality of catalytic, regenerative, reverse-flow reactors in series, the amount of unconverted alkane in the raffinate exiting the most downstream reactor can be reduced to very low amounts, e.g., less than 1% (by weight) of the raffinate, such as less than 1%. Accordingly, the low conversion of the prior art methods is overcome, without the need for recycling unconverted alkane to an upstream reactor in the system.

While the present invention has been described and illustrated with respect to certain embodiments or aspects, it is to be understood that the invention is not limited to the particulars disclosed and extends to all equivalents within the scope of the claims. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A process for converting alkane, the process comprising
a. providing a first reactant and a first oxidant, wherein the first reactant comprises ≥10.0% (molar basis) of a first alkane, wherein the first oxidant comprises molecular oxygen obtained from air and the first reactant comprises ≥99.0% (molar basis) of C2+ alkane;
b. providing a second reactant and a second oxidant, wherein the second reactant comprises ≥10.0% (molar basis) of a second alkane, wherein the second oxidant comprises molecular oxygen obtained from air and the second reactant comprises ≥99.0% (molar basis) of C2+ alkane;
c. providing a reverse-flow reactor comprising a heated first thermal mass, a second thermal mass, and at least one hydrocarbon conversion catalyst, wherein (i) the first thermal mass comprises ≥50.0 wt. % of a first sorbent, based on total weight of the first thermal mass, and/or the second thermal mass comprises ≥50.0 wt. % of a second sorbent, based on total weight of the second thermal mass and (ii) the hydrocarbon conversion catalyst comprises ≥90.0 wt. % of at least one oxydehydrogenation catalyst;
d. during a first time interval,
i. passing the first reactant and the first oxidant to the reverse-flow reactor;
ii. transferring heat from the heated first thermal mass to at least one of the first reactant or first oxidant and combining the first reactant and first oxidant to produce a first mixture, the first mixture has a C2+ alkane: molecular oxygen molar ratio in the range of 10.0 to 20.0;
iii. catalytically transferring hydrogen from the first alkane to the first oxidant at a temperature range of 650° C. to 900° C. in the presence of the hydrocarbon conversion catalyst to produce a third mixture, the third mixture comprising (A) C2+ olefin produced by the catalytic transfer and (B) any unconverted first mixture;
iv. transferring heat from the third mixture to the second thermal mass;
v. conducting at least a portion of the third mixture away from the reverse flow-reactor;
vi. lessening or discontinuing the passing of the first mixture to the reverse-flow reactor; and
e. during a second time interval,
i. passing the second reactant and second oxidant to the reverse-flow reactor;
ii. transferring heat from the heated second thermal mass to at least one of the second reactant or second oxidant and combining the second reactant and second oxidant to produce a second mixture, wherein the second mixture has a C2+ alkane:molecular oxygen molar ratio in the range of 10.0 to 20.0;
iii. catalytically transferring hydrogen from at least a portion of the second alkane to the second oxidant at a temperature range of 650° C. to 900° C. in the presence of the hydrocarbon conversion catalyst to produce a fourth mixture, the fourth mixture comprising (A) C2+ olefin produced by the catalytic transfer and (B) any unreacted second mixture;
iv. transferring heat from the fourth mixture to the first thermal mass to re-heat the first thermal mass;
v. conducting at least a portion of the fourth mixture away from the reverse flow-reactor; and
vi. lessening or discontinuing the passing of the second mixture to the reverse-flow reactor.

2. The process of claim 1, further comprising:
f. separating (A) ≥50.0% (molar basis) of the third mixture's $C_{2+}$ olefin, and/or (B) ≥50.0% (molar basis) of the fourth mixture's $C_{2+}$ olefin, to produce a raffinate and separated olefin; and
g. polymerizing at least a portion of the separated olefin.

3. The process of claim 2, further comprising separating alkane from the raffinate, wherein at least a portion of the first reactant comprises the separated alkane.

4. The process of claim 1, wherein (i) ≥50.0 wt. % of the first thermal mass, based on total weight of the first thermal mass, is located in a first region of the reverse-flow reactor, (ii) ≥50.0 wt. % of the second thermal mass, based on total weight of the second thermal mass, is located in a second region of the reverse-flow reactor, and (iii) ≥50.0 wt. % of the hydrocarbon conversion catalyst, based on the weight of the hydrocarbon conversion catalyst, is located in a third region of the reverse-flow reactor, the third region being located between the first and second regions.

5. The process of claim 1, wherein the separating of step (f) includes:
(i) sorbing at least a portion of the fourth mixture's $C_{2+}$ olefin with the first sorbent during step (e)(iv), and then desorbing at least a portion of the sorbed $C_{2+}$ olefin following step (e)(iv); and
(ii) sorbing at least a portion of the third mixture's $C_{2+}$ olefin with the second sorbent during step (d)(iv), and then desorbing at least a portion of the sorbed $C_{2+}$ olefin following step (d)(iv).

6. The process of claim 1, further comprising:
h. desorbing at least a portion of any $C_{2+}$ olefin sorbed by the second sorbent during a third interval; and
i. desorbing at least a portion of any $C_{2+}$ olefin sorbed by the first sorbent during a fourth interval; wherein the third interval follows the first interval, the second interval follows the third interval, and the fourth interval follows the second interval.

7. The process of claim 6, wherein the desorbing of step (h) includes passing a first utility fluid to the reverse-flow reactor, and transferring heat from the first utility fluid to the first and/or second sorbent, and wherein the desorbing of step (i) includes passing a second utility fluid to the reverse-flow reactor, and transferring heat from the first utility fluid to the first and/or second sorbent.

8. The process of claim 7, wherein the first utility fluid comprises ≥50.0 wt. % steam, based on total weight of the first utility fluid, and the second utility fluid comprises ≥50.0 wt. % steam, based on total weight of the second utility fluid.

9. The process of claim 1, further comprising repeating steps (d)-(e).

10. The process of claim 1, wherein the first and second time intervals are substantially non-overlapping time intervals, each being in the range of from 1 to 15 seconds.

11. An alkane conversion process, comprising:
 a. providing a first reactant and a first oxidant, wherein the first oxidant comprises molecular oxygen obtained from air and the first reactant comprises ≥99.0% (molar basis) of C2+ alkane;
 b. providing a second reactant and a second oxidant, wherein the second oxidant comprises molecular oxygen obtained from air and the second reactant comprises ≥99.0% (molar basis) of C2+ alkane;
 c. providing a reverse-flow reactor comprising a heated first thermal mass, a second thermal mass, and at least one hydrocarbon conversion catalyst, wherein the hydrocarbon conversion catalyst comprises ≥90.0 wt. % of at least one oxydehydrogenation catalyst;
 d.
  i. passing the first reactant and the first oxidant to the reverse-flow reactor;
  ii. transferring heat from the heated first thermal mass to at least one of the first reactant or first oxidant and combining the first reactant and first oxidant to produce a first mixture, the first mixture having a C2+ alkane:molecular oxygen molar ratio in the range of 10.0 to 20.0;
  iii. catalytically transferring at least a portion of the first alkane's hydrogen to the first oxidant at a temperature range of 650° C. to 900° C. in the presence of the hydrocarbon conversion catalyst to produce a third mixture, the third mixture comprising (A) C2+ olefin produced by the hydrogen transfer and (B) any unconverted first mixture;
  iv. transferring heat from the third mixture to the second thermal mass and sorbing at least a portion of the third mixture's C2+ olefin;
  v. conducting at least a portion of the third mixture away from the reverse flow-reactor;
  vi. lessening or discontinuing the passing of the first mixture to the reverse-flow reactor;
 e. desorbing at least a portion of the C2+ olefin sorbed in step (d)(iv);
 f.
  i. passing the second reactant and second oxidant to the reverse-flow reactor;
  ii. transferring heat from the heated second thermal mass to at least one of the second reactant or second oxidant and combining the second reactant and second oxidant to produce a second mixture, the second mixture having a C2+ alkane:molecular oxygen molar ratio in the range of 10.0 to 20.0;
  iii. catalytically transferring at least a portion of the second alkane's hydrogen to the second oxidant at a temperature range of 650° C. to 900° C. in the presence of the hydrocarbon conversion catalyst to produce a fourth mixture, the fourth mixture comprising (A) C2+ olefin produced by the catalytic transfer and (B) any unreacted second mixture;
  iv. transferring heat from the fourth mixture to the first thermal mass to re-heat the first thermal mass and sorbing at least a portion of the fourth mixture's C2+ olefin;
  v. conducting at least a portion of the fourth mixture away from the reverse flow-reactor;
  vi. lessening or discontinuing the passing of the second mixture to the reverse-flow reactor; and
 g. desorbing at least a portion of the C2+ olefin sorbed in step (f)(iv).

12. An alkane conversion process, comprising:
 a. providing a first reactant and a first oxidant, wherein the first oxidant comprises molecular oxygen obtained from air and the first reactant comprises ≥99.0% (molar basis) of C2+ alkane;
 b. providing a second reactant and a second oxidant, wherein the second oxidant comprises molecular oxygen obtained from air and the second reactant comprises ≥99.0% (molar basis) of C2+ alkane;
 c. providing first and second reverse-flow reactors, wherein (i) the first reverse-flow reactor comprises a heated first thermal mass, a second thermal mass, and at least one first hydrocarbon conversion catalyst, the first hydrocarbon conversion catalyst comprising ≥90.0 wt. % of at least one oxydehydrogenation catalyst, and (ii) the second reverse-flow reactor comprises a heated third thermal mass, a fourth thermal mass, and at least a second hydrocarbon conversion catalyst, the second hydrocarbon conversion catalyst comprising ≥90.0 wt. % of at least one oxydehydrogenation catalyst;
 d. passing the first reactant and first oxidant to the first reverse-flow reactor;
 e. transferring heat from the heated thermal mass of the first stage to at least one of the first reactant or first oxidant and combining the first reactant and first oxidant to produce a first mixture, the first mixture having a C2+ alkane:molecular oxygen molar ratio in the range of 10.0 to 20.0;
 f. catalytically transferring hydrogen from at least a portion of the first mixture's alkane at a temperature range of 650° C. to 900° C. in the presence of the first hydrocarbon conversion catalyst to produce a third mixture, the third mixture comprising C2+ olefin produced by the catalytic transfer and unconverted alkane of the first mixture;
 g. transferring heat from the third mixture to the second thermal mass;
 h. sorbing, in the first reactor stage, at least a portion of the third mixture's C2+ olefin with a sorbent as the heat is transferred to the second thermal mass;
 i. conducting a first raffinate stream from the first reverse-flow reactor to the second reverse-flow reactor, wherein the first raffinate stream comprises at least a portion of the third mixture's alkane;
 j. transferring heat from the heated third thermal mass to at least a portion of the first raffinate, catalytically transferring hydrogen from at least a portion of the raffinate's alkane in the presence of the second hydrocarbon conversion catalyst at an alkane:oxidant molar ratio in the range of from 1:2 to 50:1 to produce a fifth mixture comprising C2+ olefin produced by the hydrogen transfer, and transferring heat from the fifth mixture to the fourth thermal mass;

k. lessening or discontinuing the passing of the first mixture to the reverse-flow reactor;
l. passing the second reactant and second oxidant to the second stage of the reverse-flow reactor;
m. transferring heat from the heated fourth thermal mass to the second mixture at least one of the second reactant or second oxidant and combining the second reactant and second oxidant to produce a second mixture, the second mixture having a C2+ alkane:molecular oxygen molar ratio in the range of 10.0 to 20.0;
n. catalytically transferring hydrogen from at least a portion of the second mixture's alkane at a temperature range of 650° C. to 900° C. in the presence of the second hydrocarbon-conversion catalyst to produce a fourth mixture, the fourth mixture comprising C2+ olefin produced by the catalytic transfer and unconverted alkane of the second mixture;
o. transferring heat from the fourth mixture to the third thermal mass;
p. sorbing, in the second reactor stage, at least a portion of the fourth mixture's C2+ olefin with a sorbent as the heat is transferred to the third thermal mass;
q. conducting a second raffinate stream from the second reverse-flow reactor to the first reverse-flow reactor, wherein the second raffinate stream comprises at least a portion of the fourth mixture's alkane;
r. transferring heat from the heated second thermal mass to the second raffinate, and catalytically transferring hydrogen from at least a portion of the second raffinate's alkane in the presence of the first hydrocarbon conversion catalyst at an alkane:oxidant molar ratio in the range of from 1:2 to 50:1 to produce a sixth mixture comprising C2+ olefin produced by the hydrogen transfer, and transferring heat from the sixth mixture to the first thermal mass;
s. lessening or discontinuing the passing of the second mixture to the reverse-flow reactor; and
t. desorbing C2+ olefin from the first and/or second reverse-flow reactor (i) after step (k) and/or (ii) after step (s).

* * * * *